United States Patent [19]

Therien et al.

[11] Patent Number: 5,955,603
[45] Date of Patent: Sep. 21, 1999

[54] PORPHYRINS AND PORPHYRIN SYNTHESIS TECHNIQUES

[75] Inventors: Michael J. Therien, Philadelphia, Pa.; Stephen DiMagno, Lincoln, Nebr.

[73] Assignees: Trustees of the University of Pennsylvania, Philadelphia, Pa.; Board of Regents of University of Nebraska, Lincoln, Nebr.

[21] Appl. No.: 09/167,443

[22] Filed: Oct. 6, 1998

Related U.S. Application Data

[60] Division of application No. 08/352,555, Dec. 8, 1994, Pat. No. 5,817,830, and a continuation-in-part of application No. 08/234,651, Apr. 28, 1994, Pat. No. 5,599,924, which is a continuation-in-part of application No. 08/064,468, May 20, 1993, Pat. No. 5,493,017, which is a continuation-in-part of application No. 07/929,943, Aug. 14, 1992, Pat. No. 5,371,199.

[51] Int. Cl.$^6$ .................................................. C07D 487/22
[52] U.S. Cl. ........................................... 540/145; 568/910
[58] Field of Search ............................... 540/145; 568/910

[56] References Cited

U.S. PATENT DOCUMENTS

| | | | |
|---|---|---|---|
| 4,892,941 | 1/1990 | Dolphin et al. | 540/145 |
| 5,212,300 | 5/1993 | Ellis, Jr. et al. | 540/145 |

*Primary Examiner*—Richard L. Raymond
*Assistant Examiner*—Pavanaram K Sripada
*Attorney, Agent, or Firm*—Woodcock Washburn Kurtz Mackiewicz & Norris LLP

[57] ABSTRACT

Strapped porphyrins and electron-deficient porphyrins are provided, as well as processes and intermediates for their preparation. In certain embodiments, such compounds are prepared by nucleophilic displacement of leaving groups from methylpyrroles. In other embodiments, such compounds are prepared by condensing pyrrole derivatives and removing water thus formed from the resulting reaction mixture.

11 Claims, 2 Drawing Sheets

PORPHYRINS AND PORPHYRIN SYNTHESIS TECHNIQUES

RELATED APPLICATIONS

This patent application is a division of application Ser. No. 08/352,555, filed on Dec. 8, 1994 (now U.S. Pat. No. 5,817,830), which is a continuation-in-part of application Ser. No. 08/234,651, filed on Apr. 28, 1994, (now U.S. Pat. No. 5,599,924), which is a continuation-in-part of application Ser. No. 08/064,468, filed May 20, 1993, (now U.S. Pat. No. 5,493,017), which, in turn, is a continuation-in-part of application Ser. No. 07/929,943, filed Aug. 14, 1992, (now U.S. Pat. No. 5,371,199). The entire contents of these patent applications are incorporated herein by reference.

FIELD OF THE INVENTION

This invention relates to novel chiral and/or strapped porphyrins and to techniques and intermediates useful in preparing these and other types of porphyrin-based compounds.

BACKGROUND OF THE INVENTION

Porphyrins are derivatives of porphine, a conjugated cyclic structure of four pyrrole rings linked through their 2- and 5-positions by methine bridges. Porphyrins can be covalently attached to other molecules. The electronic features of the porphyrin ring system can be altered by the attachment of one or more substituents. The term "porphyrin" includes derivatives wherein a metal atom is inserted into the ring system, as well as molecular systems in which ligands are attached to the metal. The substituents, as well as the overall porphyrin structure, can be neutral, positively charged, or negatively charged.

Electron-deficient porphyrins (i.e., porphyrins bearing substituents that are electron-withdrawing relative to hydrogen) have been suggested for use as industrial oxidation and reduction catalysts. Strapped porphyrins, wherein atoms at or near the periphery of the porphyrin ring system are covalently bound through linkages (straps) that do not include the porphyrin core, also have been suggested for a variety of uses, including use as enantioselective oxidation catalysts. A number electron-deficient porphyrins and strapped porphyrins have been prepared, but many known synthetic methods generally proceed in low yield, if at all, and cannot be used to produce many types of porphyrins.

Accordingly, there exists a need in the art for efficient synthetic methods capable of producing a greater variety of electron-deficient and/or strapped porphyrins.

OBJECTS OF THE INVENTION

It is one object of the present invention to provide improved methods for synthesizing electron-deficient porphyrins.

It is another object of the invention to provide improved methods for synthesizing strapped and/or chiral porphyrins.

It is yet another object to provide novel electron-deficient porphyrins.

It is yet another object to provide novel strapped porphyrins.

It is still another object to provide synthetic precursors for electron-deficient, strapped and/or chiral porphyrins.

SUMMARY OF THE INVENTION

These and other objects are satisfied by the present invention, which provides novel processes for preparing porphyrins and novel strapped and/or electron-deficient porphyrins prepared by such processes. In certain embodiments, porphyrins are prepared by contacting a pyrrole derivative having formula (1) with a pyrrole compound having formula (2) in organic solvent for a time and under conditions effective to form a covalent linkage between the pyrrole derivative and the pyrrole.

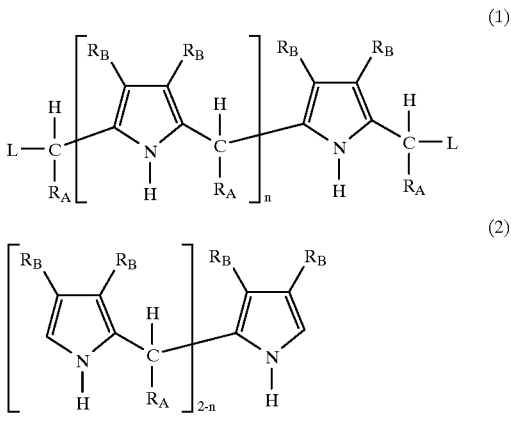

In preferred embodiments $R_A$ and $R_B$ are selected from the group consisting of H, groups that are electron-withdrawing relative to hydrogen, covalently-bound multi-atom linkages, and acid-stable chemical functional groups such that: at least one $R_A$ is H or a group that is electron-withdrawing relative to hydrogen; at least two $R_A$, together, form a covalently-bound, multi-atom linkages; at least two $R_B$, together, form a covalently-bound, multi-atom linkage; or at least one $R_A$ and at least one $R_B$, together, form a covalently-bound, multi-atom linkage. In preferred embodiments, $R_A$ has formula $CF_2R_1'$ wherein $R_1$ is alkyl, alkenyl, alkynyl, or a group having a higher formal oxidation state, such as a halogenated or perhalogenated derivative. In preferred embodiments, the multi-atom linkage includes a group that is electron-withdrawing relative to hydrogen. L is a leaving group and n preferably is 0, 1 or 2.

In further embodiments, porphyrins are prepared by reacting at least two molecules having formula (3) in organic solvent for a time and under conditions effective to form a covalent bond between said molecules.

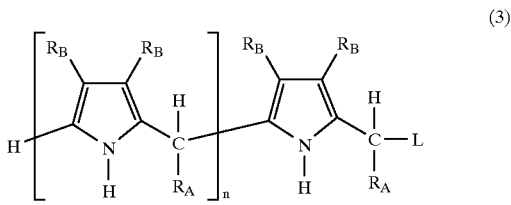

The invention also provides synthetic methods wherein an aldehyde having formula $R_A$—CHO is contacted with a pyrrole derivative having formula (4) (q=0, 1, or 2) in organic solvent in the presence of acid for a time and under conditions effective to form a reaction mixture comprising water and an adduct of the aldehyde and the pyrrole derivative, and a portion of the water thus formed is removed from said reaction mixture.

(4)

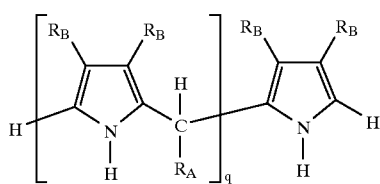

Also provided are synthetic methods wherein an alcohol having formula (5) is reacted in organic solvent in the presence of acid for a time and under conditions effective to form a reaction mixture comprising water and an adduct of the alcohol, and a portion of the water thus formed is removed from the reaction mixture.

(5)

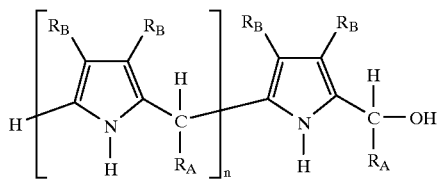

In other embodiments, porphyrins are prepared by contacting a pyrrole derivative having formula (6) with a pyrrole compound having formula (2) in organic solvent in the presence of acid for a time and under conditions effective to form a reaction mixture comprising water and an adduct of the pyrrole derivative and then removing from the reaction mixture a portion of the water thus formed.

(6)

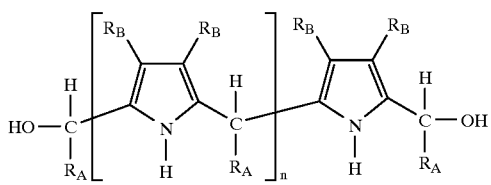

The invention also provides strapped porphyrins having formula (7), (8), or (9):

(7)

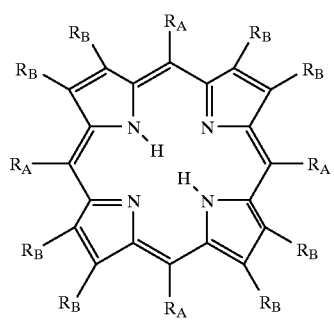

(8)

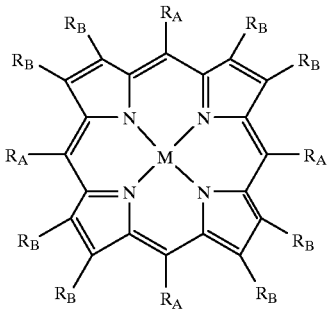

(9)

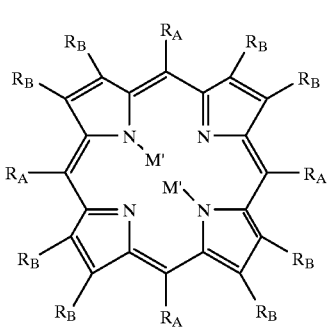

wherein M and M' are metal atoms and at least two $R_A$, at least two $R_B$, or an $R_A$ and an $R_B$, together, form a group that is electron-withdrawing relative to hydrogen. In preferred embodiments, at least two $R_A$ and/or at least two $R_B$ are alkyl having about 3 to about 35 carbon atoms, aryl having about 6 to about 40 carbon atoms, C(O)O-(alkyl) or C(O)-(alkyl).

In another aspect, the invention provides polymers comprising linked porphyrin units, at least one of such units being a strapped porphyrin. In certain embodiments, prophyrin units having formula (7), (8), or (9) share covalent bonds. In other embodiments, at least one $R_A$ group or $R_B$ group functions as a linking group. In these embodiments, at least a portion of a linking group can have formula $[C(R_C)=C(R_D)(R_E)]_x$, $[C\equiv C(R_D)]_x$, $[CH_2(R_C)-CH(R_D)(R_E)]_x$ or $[CH=CH(R_D)]_x$ where $R_C$, $R_D$, and $R_E$ are, independently, H, F, Cl, Br, I, alkyl or heteroalkyl having from 1 to about 20 carbon atoms, aryl or heteroaryl having about 4 to about 20 carbon atoms, alkenyl or heteroalkenyl having from 1 to about 20 carbon atoms, alkynyl or heteroalkynyl having from 1 to about 20 carbon atoms, trialkylsilyl or prophyrinato, provided that at least one of $R_C$, $R_D$, and $R_E$ is not H and x is at least 1. $R_C$, $R_D$, and $R_E$ also can include peptides, nucleosides, and/or saccharides. The remaining of $R_A$ and $R_B$ can be H, halogen, alkyl or heteroalkyl having 1 to about 20 carbon atoms or aryl or heteroaryl having 4 to about 20 carbon atoms, C(RC)=C($R_D$)($R_E$), C$\equiv$C($R_D$), or a chemical functional group that includes a peptide, nucleoside, and/or saccharide. In other preferred embodiments, the linking group is cycloalkyl or aryl having about 6 to about 22 carbon atoms.

The invention also provides processes for preparing porphyrin-containing polymers. In certain embodiments, the processes comprise providing at least two compounds that, independently, having formula (7), (8), or (9) wherein at least one $R_A$ group or $R_B$ group in each of the compounds contains an olefinic carbon-carbon double bound or a chemical functional group reactive therewith. In other embodiments, at least one $R_A$ group or $R_B$ group in each of the compounds contains a carbon-carbon triple bond or a chemical functional group reactive therewith. The compounds are then contacted for a time and under reaction conditions effective to form covalent bonds through the carbon-carbon double and/or triple bonds.

The porphyrins and porphyrin-containing polymers of the invention can be used, for example, as dyes, catalysts, contrast agents, antitumor agents, antiviral agents, and in chemical sensors and electrooptical devices.

BRIEF DESCRIPTION OF THE DRAWINGS

The numerous objects and advantages of the present invention may be better understood by those skilled in the art by reference to the accompanying figures, in which.

DETAILED DESCRIPTION OF THE INVENTION

Figure 1:
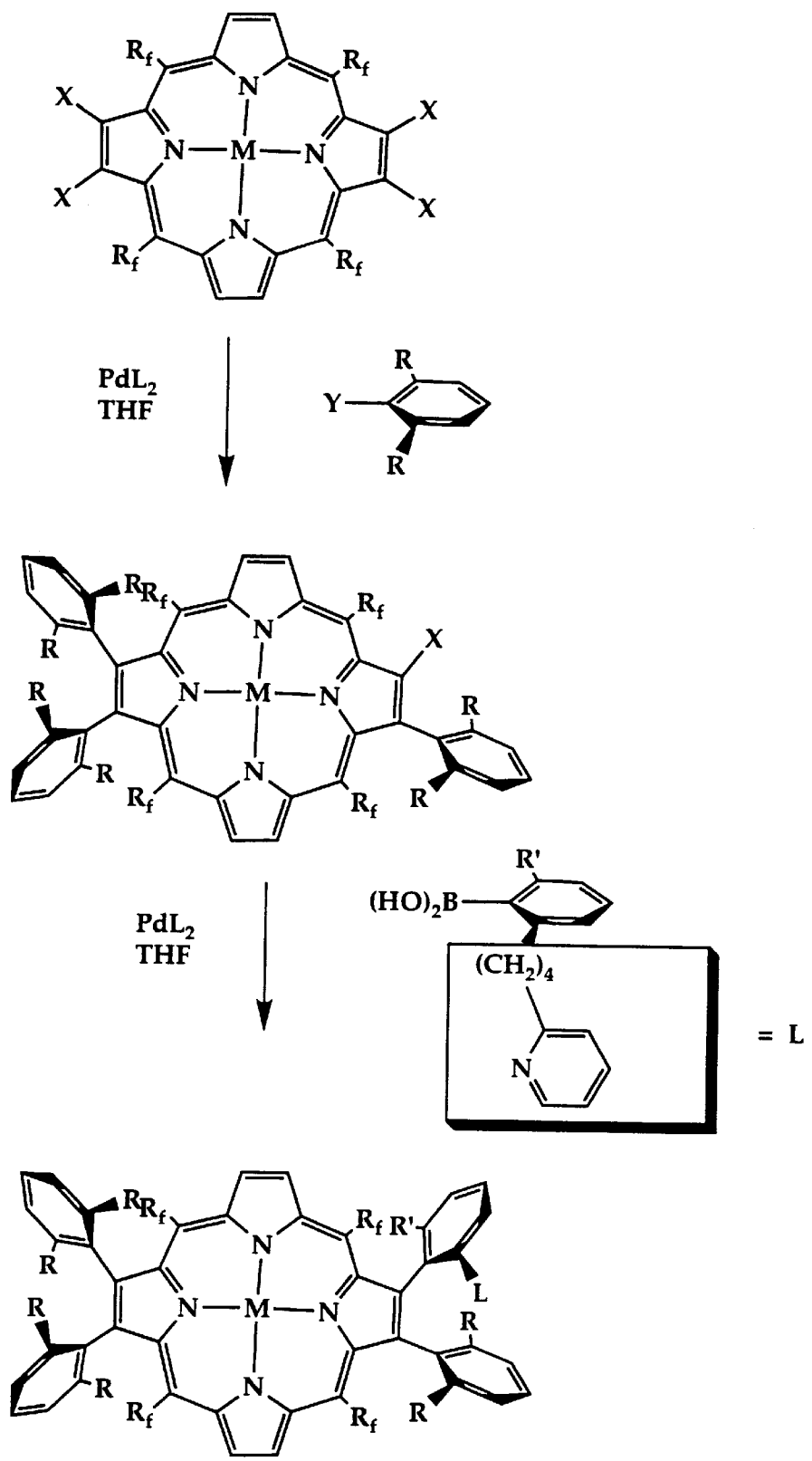
FIG. 1 shows a synthetic scheme for the preparation of chiral tetraarylporphyrins.

It has been found in accordance with the present invention that a wide variety of strapped porphyrins can be prepared by condensation of suitably functionalized pyrroles provided that at least a portion of the water of condensation is removed from the reaction mixture. In general, the resulting porphyrins have formula (7), (8), or (9) wherein M and M' are metal atoms and $R_A$ and/or $R_B$ groups, together, form a covalently-bound, multi-atom linkage. The remaining $R_A$ and $R_B$ groups can be the same or different and are selected from H and those groups known to be stable under the reaction conditions (e.g., acidic reaction conditions) under which such compounds are formed, including alkyl, alkenyl, alkynyl, and aryl groups. Representative groups are disclosed by, for example, application Ser. No. 08/064,468. Those skilled in the art will recognize that chemical protecting groups can be attached to sensitive functionality found within $R_A$ and/or $R_B$ and that such protecting groups can be removed after a particular reaction has been completed. (See e.g., Greene and Wuts in Protective Groups in Organic Synthesis, New York, John Wiley & Sons, 1991).

Compounds having formulas (7)–(9) preferably bear 1, 2, 4, 8, or 12 substituents (i.e., 1, 2, 4, 8, or 12 of $R_A$ and $R_B$ are not H). In certain embodiments, four $R_A$ groups bear electron-withdrawing functionality. In other embodiments, a single $R_B$ on each pyrryl moiety is a halogen or both $R_B$ on two non-adjacent pyrryl moieties are halogens.

Numerous examples of electron-withdrawing functional groups are known to those skilled in the art. Further, electron-withdrawing groups can be identified through routine experimentation involving, for example, replacement of hydrogen in a molecule with a given group and then testing any resultant inductive effects. Representative electron withdrawing groups include the following: $N\text{-}(alkyl)_3^-$, $NH_3^-$, $NO_2$, $SO_2\text{-}(alkyl)$, CN, $SO_2\text{-}(aryl)$, C(O)OH, F, Cl, Br, I, $CF_2R_1$, $CCl_2R_1$, $CBr_2R_1$, $CI_2R_1$, C(O)O-(alkyl), C(O)-(alkyl), and/or CHO, wherein alkyl groups have from about 1–35 carbon atoms and aryl groups have about 3–50 carbon atoms. Electron-withdrawing groups used as non-terminal substituents (e.g., those substituents that form strapping groups) may preferably include at least one chiral center. Alkyl and aryl groups found in non-terminal substituents have from about 1 to about 50 carbon atoms and about 3 to about 75 carbon atoms, respectively. Alkenyl and alkynyl groups found in non-terminal substituents have from about 2 to about 50 carbon atoms. Preferably, such alkyl, alkenyl, and alkynyl groups have from 3 to about 35 carbon atoms and such aryl groups have from about 6 to about 40 carbon atoms. More preferably, such alkyl, alkenyl, and alkynyl groups have from 6 to about 24 carbon atoms and such aryl groups have from about 8 to about 30 carbon atoms. Alkyl and aryl groups found in terminal substituents preferably have from 1 to about 20 carbon atoms and about 6 to about 20 carbon atoms, respectively. Alkenyl and alkynyl groups found in terminal substituents have from about 2 to about 20 carbon atoms. More preferably, such alkyl, alkenyl, and alkynyl groups have from 5 to about 20 carbon atoms and such aryl groups have from about 6 to about 20 carbon atoms. The terms alkyl, alkenyl, alkynyl and aryl are intended to include moieties substituted with, for example, halogens or nitro groups, as well as moieties wherein heteroatoms (e.g., N, O, S, Se, and Te) are inserted into the carbon backbone of an alkyl or aryl structure to yield, for example, an ether, thioether, and pyridinyl group. Alkyl, alkenyl, alkynyl, and aryl groups can bear substituents that include additional carbon atoms. Preferred electron-withdrawing groups are substituted and unsubstituted alkyl and aryl groups that possess net electron-withdrawing effects. Perhaloalkyl and perhaloaryl groups are particularly preferred, including perfluoroalkyl, perfluorophenyl, perfluorobenzyl, and tetrafluoropyridyl groups.

Numerous acid stable groups are known to those skilled in the art. (see, e.g., March, Advanced Organic Chemistry, 4th ed., 1992). Representative acid stable groups include halogens, $NO_2$, and CN.

M preferably is a lanthanide or actinide or a metal such as Sc, Ti, V, Cr, Mn, Fe, Co, Ni, Cu, Y, Zr, Nb, Mo, Ru, Re, Rh, Pd, Ag, La, Hf, Ta, W, Re, Os, Ir, Pt, Cd, Hg, Li or Au. More preferably, M is Cr, Mn, Fe, Co, Ni, Ru, Re, Rh, Pd, Os, Ir, Pt, or Au. M' can be a metal such as Li, Na, K, Rb, or Cs, preferably Li.

In certain embodiments, porphyrins according to the invention are prepared by synthesizing and then oxidizing suitably-substituted porphyrinogen compounds having, for example, formulas (10) and (11).

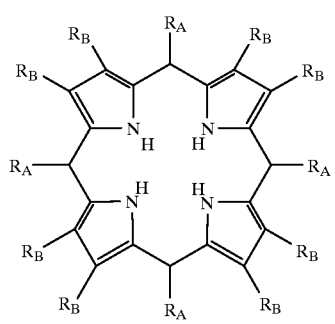

(10)

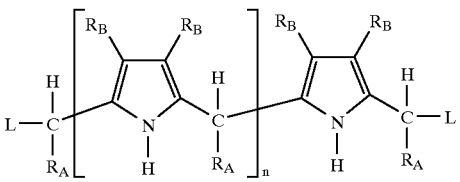

(1)

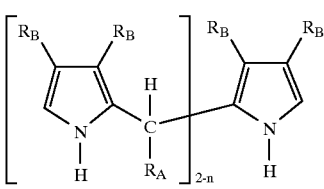

(2)

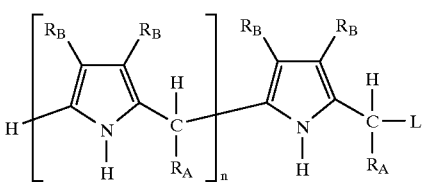

(3)

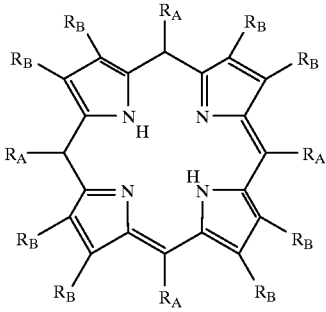

(11)

In other embodiments porphyrins are prepared by condensation and subsequent oxidation of suitably-substituted polypyrryl intermediates having, for example, formulas (12)–(15).

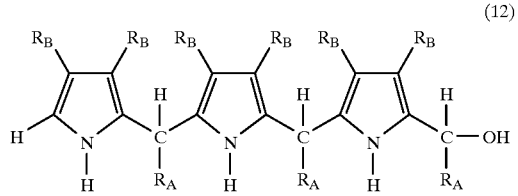

(12)

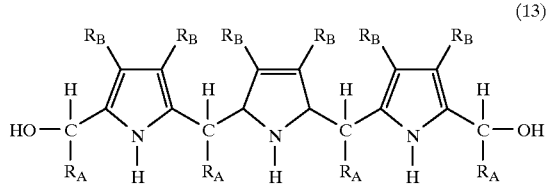

(13)

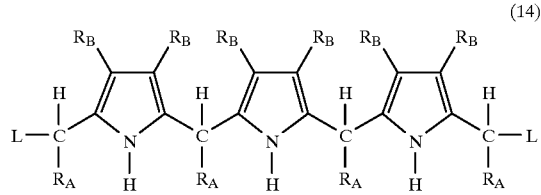

(14)

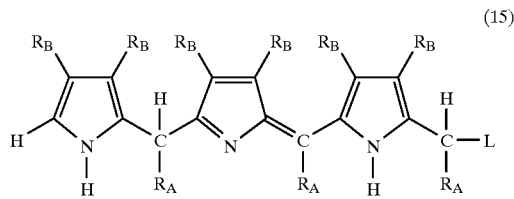

(15)

Porphyrinogens and polypyrryl intermediates can be prepared by reacting pyrrole derivatives having formula (1) with pyrrole compounds having formula (2), or by reacting at least two molecules of pyrrole derivatives having formula (3).

These reactions should be performed in organic solvent for a time and under conditions effective to form a covalent linkage between an unsubstituted 2- or 5-position in a first pyrrole compound (e.g., formula (2)) and an exocyclic methylene carbon atom in a second pyrrole compound (e.g., formula (1)). While not wishing to be bound by any particular theory, it is believed that such reactions proceed by loss of leaving group, L, from the exocyclic methylene by an $SN_1$ process. Thus, preferred L groups facilitate such reactions by, for example, readily forming stable (and, preferably, inert) anionic species. A wide variety of leaving groups can be used in accordance with the present invention, including those disclosed by Advanced Organic Chemistry, J. March, 4th ed., John Wiley & Sons, New York, 1992. Some leaving groups may need to be protonated before displacement. Preferred leaving groups include halogens, sulfates, sulfonates (e.g., methanesulfonate, trifluoromethanesulfonate, toluenesulfonate, and p-bromobenzenesulfonate), carboxylates (e.g., acetate, trifluoroacetate, and p-nitrobenzoate), and silyl ethers (e.g., trimethylsilylethers).

Condensation reactions according to the invention can be performed in a wide variety of organic solvents, including trichloroethylene, chloroform, carbon tetrachloride, benzene, toluene, xylenes, methylene chloride, dimethylsulfoxide, acetonitrile, dimethylformamide, and anisole. Aprotic solvents are preferred. In preferred embodiments, such reactions are performed between 0° C. and 130° C.

Alternatively, porphyrinogens and polypyrryl intermediates can be prepared by condensing alcohols having formula (5) (n=0, 1, or 2). Such compounds also can be prepared by condensing aldehydes having formula $R_A$—CHO with a pyrrole derivative having formula (4) (q=0, 1, or 2).

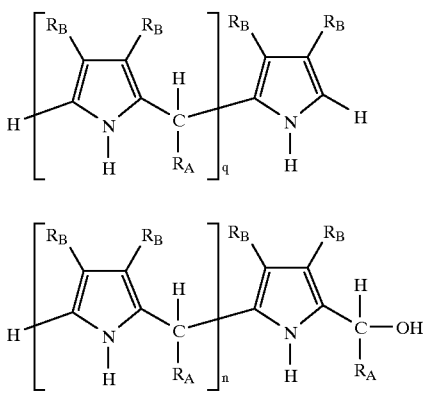

(4)

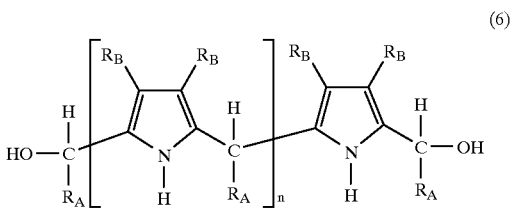

(5)

Porphyrinogens and polypyrryl intermediates alternatively can be prepared by condensing alcohols having formula (6) (n=0, 1, or 2) with pyrrole compounds having formula (2).

(6)

Each of these condensation reactions should be performed in organic solvent in the presence of acid for a time and under conditions effective to form reaction mixtures comprising water and an adduct of the reagents. In accordance with the invention, at least a portion of the water thus formed is removed from the reaction mixture.

A wide variety of organic solvents can be used in the condensation reactions of the invention, including benzene, toluene, xylenes, methylene chloride, chloroform, trichloroethylene, and mixtures thereof. Aprotic solvents are preferred, particularly nonpolar, aprotic solvents. Solvents capable of forming azeotropes (i.e., constant boiling mixtures) with water are particularly preferred. In preferred embodiments, condensation reactions are performed between 35° C. and 110° C.

Acids according to the invention are ions or molecules having the capacity to accept at least one electron pair. Representative acids include benzoic acid, sulfonic acids (e.g., p-toluenesulfonic acid and methanesulfonic acid), trifluoroacetic acid, boron trifluoride, boron trichloride, and mixtures thereof. Preferred acids are not volatile under reactions conditions of the invention. Protic acids, particularly strong protic acids (i.e., those having $pK_a<0$), are preferred. In preferred embodiments, a catalytic (i.e., non-stoichiometric) amount of acid is used.

Water can be removed from adduct-containing reaction mixtures by a wide variety of known techniques, including membrane-based separations. Water also can be removed by contacting a reaction mixture with moieties that absorb, trap, or react with water or otherwise render water non-reactive. In general, the chosen technique should remove at least a portion or any water present but should not remove the adduct-forming reagents. Representative water removal techniques are disclosed by U.S. Pat. No. 4,332,643 (Reid), European Patent Application EP 92-114390 (Inaba, et al.), Japanese Patent Applications 91-146674 (Miyazaki, et al.), 91-20083 (Kondo, et al.), and 90-104128 (Okazaki, et al.), and Brazilian Patent Application 77-433 (Scaglia, et al.). Water preferably is removed by distilling an azeotrope formed by the water and the organic solvent. In certain embodiments, the distilled azeotrope is collected in a vessel and allowed to separate into aqueous and organic phases, and the organic (solvent) phase is returned to the reaction mixture. In other embodiments, the distilled azeotrope is contacted with a drying agent and the dried distillate is returned to the reaction mixture. Representative drying agents include phosphorous pentoxide, calcium hydride, calcium oxide, barium oxide, lithium aluminum hydride, molecular sieves, and mixtures thereof. Numerous additional drying agents are well-known to persons of ordinary skill in the art. In further embodiments, the dried distillate is collected and a roughly equal volume of fresh solvent is added to the reaction mixture. In still further embodiments, semi-permeable membrane technology is used to remove water from the reaction mixture as it is formed.

Compounds having formulas (4)–(6) preferably prepared by contacting a pyrrole having formula (2) with base with or without organic solvent in the presence of aldehydes having formula $R_A$—CHO. Representative bases include sodium hydroxide, lithium hydroxide, potassium hydroxide, barium hydroxide, alkyl or aryl lithium reagents, and alkyl or aryl Grignard reagents, with sodium hydroxide being preferred. Representative solvents include tetrahydrofuran, ethers, alcohols, water, dimethylsulfoxide, and dimethylformamide. In preferred embodiments, such reactions are performed between −78° C. and 30° C. The pyrrole, aldehyde, and base can be reacted simultaneously or in a number of different ways. For example, the pyrrole can be contacted with base and then added to the aldehyde or it can be contacted with base in the presence of aldehyde. In certain embodiments, pyrrole, aldehyde, and base are contacted in the absence of solvent. The product produced depends, in part, upon the proportions of pyrrole and aldehyde used. For example, the use of excess pyrrole tends to favor formation of compound (4), the use of excess aldehyde tends to favor formation of compound (6), and the use of equimolar proportions tends to favor formation of compound (5).

Compounds having formulas (1) and (2) preferably are prepared by reacting hydroxymethylpyrroles having formulas (5) and (6) with suitable derivatizing reagents, preferably in organic solvent and in the presence of base. Representative bases include trimethylamine, triethylamine, pyridine, dimethylaminopyridine, and 1,8-bis(dimethylamino) naphthalene, N,N,N',N'-tetramethyl-1,8-naphthalenediamine(Proton-Sponge®, Aldrich Chemical Co.). Representative solvents include methylene chloride, chloroform, and tetrahydrofuran. In preferred embodiments, such reactions are performed between 0° C. and 25° C. A wide variety of useful derivatizing reagents are known in the art. Preferred derivatizing reagents react with the hydroxyl oxygen atom to produce leaving group L. Representative of such derivatizing reagents are the sulfonyl halides, silyl halides, acid halides, and acid anhydrides.

Oxidation of porphyrinogens and polypyrryl intermediates can be accomplished by a number of techniques. For example, porphyrinogen- and/or polypyrryl-containing reaction mixtures can be exposed to oxidizing conditions. Alternatively, such compounds are isolated from a reaction mixture and then contacted with an oxidizing agent. Representative oxidizing agents include oxygen, p-chloranil, 2,3-dichloro-5,6-dicyanobenzoquinone (DDQ), and mixtures. Oxidation of electron-deficient compounds also can be effected using bulk electrochemical methods (see e.g., Laboratory Techniques in Electroanalytical Chemistry, P. T. Kissinger and W. R. Heineman, eds., New York, Marcel Dekker, 1984). In general, oxidation conditions for partially-oxidized porphyrinogens and polypyrryl intermediates (e.g., formulas (11), (13), and (15)) will be less vigorous than for porphyrinogens and polypyrryl intermediates in more reduced form (e.g., formulas (10), (12), and (14)). More electron-deficient porphyrinogens generally require more vigorous oxidation conditions. In preferred embodiments, oxidation reactions are performed between 25° C. and 150° C.

The processes of the invention produce somewhat monomeric compounds that can be incorporated into porphyrin-containing homopolymers or copolymers or into macromolecular or supramolecular species containing, for example, one or more peptides, nucleosides, or saccharides. Polymers according to the invention can contain as few as 2 porphyrin units, but more preferably contain at least 3 porphyrin units, more preferably at least 5 porphyrin units. In certain embodiments, polymers of the invention comprise a plurality or porphyrin units that, independently, have formula (7), (8), or (9) wherein at least one $R_A$ group or $R_B$ group includes a linking group selected from $[C(R_C)=C(R_D)(R_E)]_x$, $[C{\equiv}C(R_D)]_x$, $[CH_2(R_C)-CH(R_D)(R_E)]_x$ or $[CH{=}CH(R_D)]_x$ where x is at least 1. The remaining $R_A$ and $R_B$ include at least one group that is electron-withdrawing relative to hydrogen.

In other embodiments, polymers according to the invention comprise a plurality of porphyrin units that, independently, have formula (7), (8), or (9) wherein at least one $R_A$ group or $R_B$ group is a cycloalkyl, cycloalkenyl, aryl or heteroaryl linking group having about 6 to about 22 carbon atoms.

Those skilled in the art will recognize the wide variety of polymers that can be prepared from the porphyrin-containing compounds of the invention. In certain embodiments, cofacial polymers are formed having, for example, formula (16). (See, e.g., Durand, et al., *J. Am. Chem. Soc.*, 1983, 105, 2710).

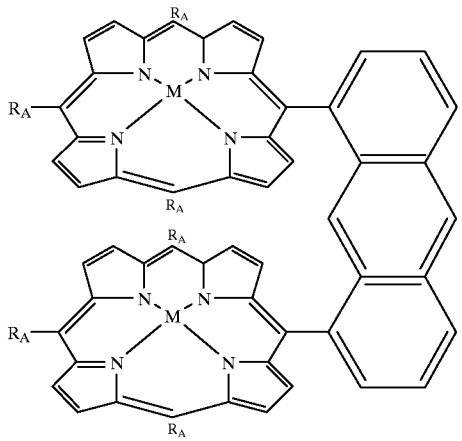

(16)

In other embodiments, somewhat linear polymer chains are formed wherein a portion of the polymer has general formula $(P_N)_r$ wherein $P_N$ is a porphyrin unit and r is at least 2. In further embodiments, linear polymer chains have general formula:

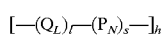

where $Q_L$ is a linking group, $P_N$ is a porphyrin unit, and h, l, and s are independently selected to be at least 1. For example, a portion of such polymers can have formula:

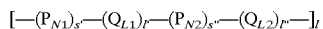

wherein $P_{N1}$ and $P_{N2}$ are independently selected porphyrin units, $Q_{L1}$ and $Q_{L2}$ are independently selected linking groups, and l', l", s', and s" are at least 1. These essentially linear polymer chains can be cross-linked such that a portion of the polymer has general formula:

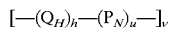

wherein $Q_H$ is a linking group, and h, u, and v are independently selected to be at least 1. A portion of these cross-linked polymers can have formula:

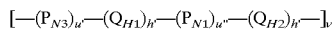

wherein $P_{N3}$ is a porphyrin unit, $Q_{H1}$ and $Q_{H2}$ are independently selected linking groups, and h', h", u', and u" are at least 1. Thus, cross-linked polymers can have formulas:

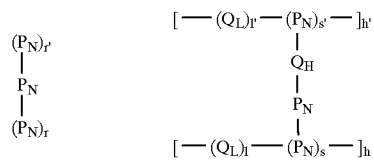

where r' is at least 1.

The polymers of the invention can be formed by contacting a substituted porphyrin with a second compound containing functionality that is reactive with the functionality contained within the porphyrin. Preferably, the porphyrin contains an olefinic carbon-carbon double bond, a carbon-carbon triple bond or some other reactive functionality. The contacting should be performed under conditions effective to form a covalent bond between the respective reactive functionalities. Preferably, porphyrin-containing polymers are formed by metal-mediated cross-coupling of, for example, dibrominated porphyrin units. Also, porphyrin-containing polymers can be synthesized using known terminal alkyne coupling chemistry. (See. e.g., Patai, et al., The Chemistry of Functional Groups, Supplement C, Part 1, pp. 529–534, Wiley, 1983; Cadiot, et al., Acetylenes, pp. 597–647, Marcel Dekker, 1964; and Eglinton, et al., *Adv. Org. Chem.*, 1963, 4, 225) As will be recognized, the second compound noted above can be a substituted porphyrin of the invention or some other moiety such as an acrylate monomer. Thus, a wide variety of copolymeric structures can be synthesized with the porphyrins of the invention. Through careful substituent selection the porphyrins of the invention can be incorporated into virtually any polymeric matrix known in the art, including but not limited to polyacetylenes, polyacrylates, polyolefins, polyethers, polyurethanes, polycarbonates, polyanilines, polypyrroles, and polythiophenes. For example, fluorescent porphyrins can be incorporated into such polymers as end-capping groups.

The porphyrins and porphyrin-containing polymers of the invention can be used, for example, as dyes, catalysts, contrast agents, antitumor agents, antiviral agents, liquid crystals, in chemical sensors and in electrooptical and solar energy conversion devices. One preferred use for compounds containing electron-deficient porphyrins are as catalysts for the oxygenation of alkanes and/or alkenes, particularly oxygenations performed in supercritical carbon dioxide. Electron-deficient porphyrins also can be incorporated into supramolecular structures. The polymers and supramolecular structures, which anchor porphyrin units in a relatively stable geometry, should improve many of the known uses for porphyrins and even provide a number of new uses, such as in a solid phase system for sterilizing virus-containing solutions. Representative uses are disclosed by, for example, the following patents, which are incorporated herein by reference: U.S. Pat. No. 4,895,682 (Ellis, et al.); U.S. Pat. No. 4,986,256 (Cohen); U.S. Pat. No. 4,668,670 (Rideout, et al.); U.S. Pat. No. 3,897,255 (Erickson); U.S. Pat. No. 3,899,334 (Erickson); U.S. Pat. No. 3,687,863 (Wacher); U.S. Pat. No. 4,647,478 (Formanek, et al.); and U.S. Pat. No. 4,957,615 (Ushizawa, et al.). Further uses are disclosed are disclosed by, for example, U.K. Patent Application 2,225,963 (Casson, et al.); International Application WO 89/11277 (Dixon, et al.); International Application WO 91/09631 (Matthews, et al.); European Patent Application 85105490.8 (Weishaupt, et al.); European Patent Application 90202953.7 (Terrell, et al.); European Patent Application 89304234.1 (Matsushima, et al.); Lehn, *Angew. Chem. Int. Ed. Engl.*, 1988, 27, 89; Wasielewski, *Chem. Rev.*, 1992, 92, 435; Mansury, et al., *J. Chem. Soc., Chem. Comm.*, 1985, 155; Groves, et al., *J. Am. Chem. Soc.*, 1983, 105, 5791; and Giroud-Godquin, et al., *Angew. Chem. Int. Ed. Engl.*, 1991, 30, 375. It is believed that the porphyrins of the invention can be substituted for the porphyrins disclosed in each of the foregoing publications.

Additional objects, advantages, and novel features of this invention will become apparent to those skilled in the art upon examination of the following examples thereof, which are not intended to be limiting. Unless otherwise stated, all reactions are performed using dry solvents under inert atmospheres. Porphyrin-forming condensation reactions are all assumed to be carried out using continuous water removal methods.

Example 1

Preparation of 2-(2',2',3',3',4',4',4'-Heptafluoro-1'-hydroxybutyl)pyrrole from Heptafluorobutyraldehyde Hydrate Heptafluorobutyraldehyde hydrate (9.26 g, 42.9 mmol) was placed in a 100 mL Schlenk flask. This was frozen with liquid nitrogen and an inert atmosphere was established. Against an outflow of nitrogen, dried pyrrole (5.95 mL, 85.8 mmol) and sodium hydroxide (4.52 g, 113 mmol) were added. The flask was wrapped in foil and the mixture was stirred overnight, during which time it solidified. A colorless liquid also was present. The volatiles were removed by vacuum, leaving a light brown solid. The solid was dissolved in 40 mL of water and the solution was extracted (4×50 mL) with methylene chloride. The organic layers were dried over sodium sulfate and then evaporated to dryness under vacuum to give 5.39 g (47%) of a light yellow-brown solid. $^1$H NMR, (CDCl$_3$, 360 MHz) d 8.50 br 1H; 6.87 m 1H; 6.32 m 1H; 6.22 m 1H; 5.28 d, J=8.17 Hz; 5.23 d, J=7.67 Hz; 2.42 br s.

Example 2

Preparation of 2-(2',2',3',3',4',4',4'-Heptafluoro-1'-hydroxybutyl)pyrrole from Using Organolithium Reagents Dry, distilled pyrrole (80 mmol) is dissolved in diethyl ether (200 ml) and cooled to −78° C. Butyl lithium (80 mmol, 32 ml of 2.5 M solution in hexane) is added dropwise with stirring and the solution is gradually warmed to room temperature with evolution of hydrogen. This solution is transferred dropwise by cannula to a −78° C. solution of dry heptafluorobutyraldehyde (previously distilled from P$_2$O$_5$) in tetrahydrofuran (THF). The solution is warmed to room temperature with stirring. The volatiles are removed by vacuum leaving a solid that is dissolved in 40 mL of water and extracted (4×50 ml) with methylene chloride. The organic layers are dried over sodium sulfate and then evaporated to dryness under vacuum to give the product.

Example 3

Preparation of 2,5-Bis(2',2',3',3',4',4',4'-heptafluoro-1'-hydroxybutyl)pyrrole

Heptafluorobutyraldehyde hydrate (5.0 g, 23 mmol) was placed in a 100 mL Schlenk flask. This was frozen with liquid nitrogen and an inert atmosphere was established. Against an outflow of nitrogen, dried pyrrole (0.694 mL, 10 mmol) and sodium hydroxide (2.25 g, 56 mmol) were added. The flask was wrapped in foil and the mixture was stirred for 2 days. The volatiles were removed by vacuum, leaving a light brown, oily solid. The solid was dissolved in 40 mL of water and the solution was extracted (4×50 ml) with methylene chloride. The organic layers were dried over sodium sulfate and then evaporated to dryness under vacuum to an oily brown solid (38%), which proved to be a diastereomeric mixture of the desired products. 1H NMR of recrystallized product (CDCl$_3$, 360 MHz) d 8.78 (broad s, 1 H); 6.28 (d, 2H, J=2.8 Hz); 5.128 (dd, 2 H, J1=117 Hz, J2=8 Hz); 2.53 (broad s, 2 H).

Example 4

Preparation of 2-(2',2'-Difluoro-2'-pentafluorophenyl-1'-hydroxyethyl)pyrrole

2-Pentafluorophenyl-2,2-difluoroethanal (40 mmol) and THF (5 ml) are placed in a 100 ml Schlenk flask. This is frozen with liquid nitrogen and an inert atmosphere is established. Against an outflow of nitrogen, dried pyrrole (5.95 mL, 85.8 mmol) and sodium hydroxide (4.52 g, 113 mmol) is added. The flask is wrapped in foil and the mixture is stirred overnight. The volatiles are removed by vacuum, the resulting solid is dissolved in 40 mL of water, and the solution is extracted (4×50 ml) with methylene chloride. The organic layers are dried over sodium sulfate and then evaporated to dryness under vacuum to give 2-(2,2-difluoro-2-pentafluorophenyl-1-hydroxyethyl)pyrrole.

Example 5

Preparation of 2-(2',2',2'-Trifluoro-1'-hydroxyethyl)pyrrole

The procedure of Example 4 is repeated except that trifluoroacetaldehyde is used in place of 2-Pentafluorophenyl-2,2-difluoroethanal.

Example 6

Preparation of 1-Pyrrolyl-1-perfluoroundecyl Methanol

The procedure of Example 4 is repeated except that perfluorododecanal is used in place of 2-Pentafluorophenyl-2,2-difluoroethanal.

Example 7

Preparation of Tetrakis(heptafluoropropyl)porphyrin from 1-Pyrrolyl-1-perfluoropropyl-Methanol Benzene (650 ml) was placed in a one liter, double-necked flask and azeotripically dried under nitrogen using a recycling Dean-Stark apparatus. p-Toluenesulfonic acid hydrate (50 mg) was added to the benzene and azeotropic distillation was continued until the distillate stopped phase separating. The Dean-Stark trap was emptied and 4 Å molecular sieves (20 ml) were added to the trap. Distillation was continued for 10 minutes with the distillate recycling through the molecular sieves. 2-Pyrrolylperfluoropropylmethanol (265 mg, 1 mmol) was dissolved in 10 ml of dry benzene and added (all at once) to the benzene solution heated at reflux. The solution became pink immediately after the addition, then gradually darkened. Heating was continued for 30 minutes and the reaction mixture was quenched with 600 mg of DDQ. Heating was continued for an additional hour under $N_2$. The solution was transferred to a 1 liter round bottom flask and the solvent was removed and recovered by rotary evaporation. The remaining dark brown residue was dissolved, to the extent possible, in 50 ml of warm hexane containing 1 ml of pyridine, and was poured directly on to a short (2×10 cm) column consisting of silica that was packed in hexane and topped with a 2 cm pad of Celite. Elution of the porphyrin was carried out with hexane. Collection was continued until the eluant became nearly colorless. The solvent was removed from the collected fraction and the resulting solid was washed with cold hexane (10 ml) and filtered to yield 90 mg (37%) of nearly pure 5,10,15,20-tetrakis(perfluoropropyl)porphyrin. An analytical sample was recrystallized from chloroform (−20° C.) to yield crystals suitable for X-ray diffraction. $^1$H NMR (360 mHz, $CDCl_3$) d 9.50 (s, 8 H); −2.30 (s, 2 H). $^{19}$F NMR ($DCDl_3CF_3COOH$ ext. std) d −79.7 (t, 3 F); −80.9 (broad s, 2 F); −118.8 (broad s, 2 F). The $^{19}$F spectrum shows evidence of exchange behavior. The signal at −118.8 ppm sharpens to a broadened triplet upon warming the solution to 55° C. $^{13}$C NMR (75 MHz, $CDCl_3$) gave only two discernable signals at 144.2 and 133.8 after a 16 hour run.

Example 8

Preparation of Tetrakis(heptafluoropropyl)porphyrin from Pyrrole and Heptafluorobutyraldehyde In a procedure analogous to that described in Example 7, the apparatus was charged with benzene (650 ml), p-toluenesulfonic acid hydrate (50 mg) and heptafluorobutyraldehyde hydrate (0.22 g, 1 mmol). After refluxing the mixture for 1 hour, dry pyrrole (70 µl, 1 mmol) was added. The reaction was monitored by thin layer chromatography (TLC); after 1.5 hours the reaction was quenched as in Example 7. The reaction mixture was neutralized with pyridine, filtered through silica gel, pumped dry, and further purified by chromatography on silica. Several pyrrole-containing products can be isolated from this preparation. The desired product, tetrakis(heptafluoro)porphyrin, eluted as the first colored band. This method give 4 mg (1.6%) of the target porphyrin.

Example 9

Preparation of Tetrachloroporphine

Porphine (Zn) (40 mg) was dissolved in 300 mL of a 1:1 mixture of THF and $CHCl_3$, and the mixture was placed in a 500 ml round bottomed flask. N-Chlorosuccinimide (NCS) was added (4.2 eq.) and the mixture was stirred overnight protected from the light. The reaction was monitored by TLC and four intermediates were observed, presumably the target compound and the mono-, di-, and trichloro intermediates. After 24 hours the reaction was stopped and tetrachloroporphine (>80%) was isolated.

Example 10

Preparation of Cofacial Porphyrin Dimers

To a THF solution of 5-bromo-10,15,20-trichloroporphyrinate (Zn) (1 eq.) is added Pd bis (triphenylphosphine) (5 mol %) and anthracene-1,8-bis (chlorozinc) (0.5 eq). The reaction is stirred for 24 hours at room temperature. One band is evident by TLC of the reaction mixture. The compound is purified by silica gel chromatography to isolate the dimeric, anthracene bridged compound.

Example 11

Preparation of 1,8-(2',5'-pyrrolyl)-1,8-hydroxy-2,2, 3,3,4,4,5,5,6,6-dodecafluorooctane Pyrrole (4.0 mmol) and 2,2,3,3,4,4,5,5,6,6,7,7-dodecafluoro-1,8-octanedicarboxaldehyde (20 mmol) are dissolved in 50 ml of THF. Sodium hydroxide (120 mmol) is added as pellets. The mixture is stirred at room temperature for one week. The solvent is removed in vacuo and the remaining solid is extracted from water with 3×50 ml of methylene chloride. The organic layer is dried over sodium sulfate and filtered, and the solvent is removed in vacuo, leaving the α,α'-perfluoroalkyl-strapped pyrrole and some polymeric side products. The mixture is purified on silica using hexane/diethyl ether as eluent. The product is isolated and the solvent is removed to leave the desired strapped pyrrole.

Example 12

Preparation of 2,5-Bis(2',2',3',3',4',4',4'-heptafluoro-1'-trimethylsiloxybutyl)pyrrole Recrystallized 2,5-bis(2',2',3',3',4',4',4'-heptafluoro-1'-hydroxybutyl)pyrrole (0.5 mmol, 0.2316 g) was dissolved in 25 ml of dry THF and transferred to a cooled (0° C.) suspension of sodium hydride (1.0 mmol, 0.024 g) in 60 mL of THF. When hydrogen evolution ceased (after 1 hour) trimethylsilyl chloride (1 mmol, 0.109 g) was added by syringe. The mixture became cloudy and was stirred at room temperature for 1 hour before the solvent was removed in vacuo. The remaining residue was partitioned between 10% sodium bicarbonate solution and pentane. The organic layer was washed twice with water and dried over magnesium sulfate, filtered and evaporated to leave a colorless oil (0.204 g, 0.34 mmol, 67%). 1H NMR ($CDCl_3$, 360 MHz) 8.68 (broad s, 1 H); 6.15 (d, 2 H, J=2.7 Hz); 5.13 (dd, 2 H, J1−18.8 Hz, J2=5.0 Hz); 0.03 (s, 18 H).

Example 13

Preparation of 2-(2',2',3',3',4',4',4'-heptafluoro-1'-trimethylsiloxybutyl)pyrrole A solution of 2-(2',2',3',3',4',4',4'-heptafluoro-1'-hydroxybutyl)pyrrole (2.6514 g, 10 mmol) dissolved in 25 ml of dry THF was transferred by canula to a suspension of sodium hydride (0.2640 g, 11 mmol) in 50 ml of THF. The mixture was stirred for 2 hours at room temperature. Trimethylsilyl chloride (1.195 g, 11 mmol) was added dropwise and the solution was stirred overnight. The resulting suspension was evaporated almost to dryness and 50 ml of water was added. The mixture was extracted 3×50 mL with pentane and the organic layers were combined and dried over magnesium sulfate. Upon standing the $MgSO_4$ withdraw a brown impurity from solution leaving a colorless organic layer. The solvent was evaporated leaving a light brown oil (3.128 g). 1H NMR showed that the crude material was 96% product by weight. The overall yield was therefore calculated to be 89%. 1H NMR (CDCl$_3$, 360 MHz) 8.43 (broad s, 1 H); 6.83 (m, 1 H); 6.22 (m, 1 H) 6.17 (q, 1 H, J=2.8 Hz) 5.16 (dd, 1 H, J1=18.5 Hz, J2=5.8 Hz); 0.03 (s, 9 H).

Example 14

Preparation of 5,10,15,20-Tetrakis(perfluoropropyl) porphyrin from 2,5-Bis(2',2',3',3',4',4',4'-heptafluoro-1'-trimethylsilyloxybutyl)pyrrole A solution containing 2,5-bis(2',2',3',3',4',4',4'-heptafluoro-1'-trimethylsilyloxybutyl)pyrrole (0.204 g, 0.34 mmol), pyrrole (0.024 ml, 0.34 mmol) in 70 ml of methylene chloride was transferred to a flask containing anhydrous p-toluenesulfonic acid (50 mg). Aliquots were withdrawn periodically and oxidized by DDQ. TLC on the oxidized aliquots were developed using hexane as the eluant. The reaction was stirred for 12 hours, during which the yield of porphyrin appeared to level off. The solution was oxidized with DDQ, neutralized with pyridine, and the solvents were evaporated. The remaining residue was dissolved in hexane (to the extent possible) and chromatographed on silica using hexane as eluant. The first band was collected and evaporated to dryness leaving the title compound (15 mg, 9.1%).

Example 15

A. Preparation of 3,4-dibromo-2,5-bis(2',2',3',3',4',4',4'-heptafluoro-1'-hydroxybutyl)pyrrole A solution of 2,5-bis(2',2',3',3',4',4',4'-heptafluoro-1'-hydroxybutyl)pyrrole (5.0 mmol, 2.32 g) dissolved in 40 ml of dry THF containing 5 ml of pyridine was treated with solid N-bromosuccinimide (NBS; 1.78 g, 10 mmol). the mixture was stirred for 2 hours at room temperature and the solvents were evaporated. The remaining solid was treated with aqueous sodium bicarbonate solution and diethyl ether and separated. An additional extraction was carried out with 50 ml of ether. The organic layers were dried over sodium sulfate and the solvent was evaporated to leave an oily solid. The solid was extracted with cold pentane (3×10 ml) leaving behind the succinimide. The pentane extracts were combined and evaporated leaving 3,4-dibromo-2,5-bis(2',2',3',3',4',4',4'-heptafluoro-1'-hydroxybutyl)pyrrole in 89% yield. 1H NMR (CDCl$_3$, 360 MHz) 9.33 (broad s, 1 H); 5.43 (dd, 2 H, J1=17.5, J2=5.6 Hz); 3.30 (broad s, 2 H).

B. Preparation of 3,4-dichloro-2,5-bis(2',2',3',3',4',4',4'-heptafluoro-1'-hydroxybutyl)pyrrole The procedure of Example 15A is repeated, except that N-chlorosuccinimide (NCS) is used in place of NBS.

C. Preparation of 3,4-diiodo-2,5-bis(2',2',3',3',4',4',4'-heptafluoro-1'-hydroxybutyl)pyrrole The procedure of Example 15A is repeated, except that N-iodosuccinimide (NIS) is used in place of NBS.

Example 16

A. Preparation of 3,4-dibromo-2,5-bis(2',2',3',3',4',4',4'-heptafluoro-1'-trimethylsilyloxybutyl)pyrrole 3,4-Dibromo-2,5-bis(2',2',3',3',4',4',4'-heptafluoro-1'-hydroxybutyl)pyrrole (1 mmol, 0.62 g) was dissolved in 25 ml of dry THF and transferred to a cooled (0° C.) suspension of sodium hydride (2.0 mmol, 0.048 g) in 100 mL of THF. When hydrogen evolution ceased (after 2 hours) trimethylsilyl chloride (2 mmol, 0.218 g) was added by syringe. The mixture was stirred at room temperature overnight before the solvent was removed in vacuo. The remaining residue was partitioned between 10% sodium bicarbonate solution and ether and the organic layer was dried over magnesium sulfate, filtered and evaporated to leave a brown oil. The product was purified by chromatography on silica gel using hexane as eluant. The product was the first material off the column (r$_f$=0.5) The fractions containing this spot were evaporated to leave a colorless oil which solidified upon cooling under vacuum to leave 3,4-dibromo-2,5-(bis(2',2',3',3',4',4',4'-heptafluoro-1'-trimethylsilyloxybutyl)pyrrole as white needles. (380 mg, 50% yield) 1H NMR (360 MHz, CDCl$_3$) 8.84 (broad s, 1 H); 5.30 (dd, 2 H, J1=19.5, J2=1.0); 0.06 (s, 18 H).

B. Preparation of 3,4-dichloro-2,5-bis(2',2',3',3',4',4',4'-heptafluoro-1'-trimethylsilyloxybutyl)pyrrole The procedure of Example 16A is repeated, except that 3,4-dichloro-2,5-bis(2',2',3',3',4',4',4'-heptafluoro-1'-hydroxybutyl)pyrrole is used in place of 3,4-bromo-2,5-bis (2',2',3',3',4',4',4'-heptafluoro-1'-hydroxybutyl)pyrrole.

C. Preparation of 3,4-diiodo-2,5-bis(2',2',3',3',4',4',4'-heptafluoro-1'-trimethylsilyloxybutyl)pyrrole The procedure of Example 16A is repeated, except that 3,4-diiodo-2,5-bis(2',2',3',3',4',4',4'-heptafluoro-1'-hydroxybutyl)pyrrole is used in place of 3,4-bromo-2,5-bis (2',2',3',3',4',4',4'-heptafluoro-1'-hydroxybutyl)pyrrole.

Example 17

A. Preparation of 3-bromo-2,5-bis(2',2',3',3',4',4',4'-heptafluoro-1'-hydroxybutyl)pyrrole The reaction is carried out as in Example 15A except that 1 equivalent of NBS is added instead of 2 equivalents.

B. Preparation of 3-chloro-2,5-bis(2',2',3',3',4',4',4'-heptafluoro-1'-hydroxybutyl)pyrrole The reaction is carried out as in Example 15B except that 1 equivalent of NCS is added instead of 2 equivalents.

C. Preparation of 3-iodo-2,5-bis(2',2',3',3',4',4',4'-heptafluoro-1'-hydroxybutyl)pyrrole The reaction is carried out as in Example 15C except that 1 equivalent of NIS is added instead of 2 equivalents.

Example 18

A. Preparation of 3-bromo-2,5-bis(2',2',3',3',4',4',4'-heptafluoro-1'-trimethylsilyloxybutyl)pyrrole The reaction is carried out as in Example 16A except that the starting pyrrole is 3-bromo-2,5-bis(2',2',3',3',4',4',4'-heptafluoro-1'-hydroxybutyl) pyrrole.

B. Preparation of 3-chloro-2,5-bis(2',2',3',3',4',4',4'-heptafluoro-1'-trimethylsilyloxybutyl)pyrrole The reaction is carried out as in Example 16B except that the starting pyrrole is 3-chloro-2,5-bis(2',2',3',3',4',4',4'-heptafluoro-1'-hydroxybutyl) pyrrole.

C. Preparation of 3-iodo-2,5-bis(2',2',3',3',4',4',4'-heptafluoro-1'-trimethylsilyloxybutyl)pyrrole The reaction is carried out as in Example 16C except that the starting pyrrole is 3-iodo-2,5-bis(2',2',3',3',4',4',4'-heptafluoro-1'-hydroxybutyl) pyrrole.

Example 19

A. Preparation of 2,3,12,13-tetrabromo-5,10,15,20-tetrakis(perfluoropropyl)porphyrin A solution containing 3,4-dibromo-2,5-bis(2',2',3',3',4',4',4'-heptafluoro-1'-trimethylsilyloxybutyl)pyrrole (0.34 mmol), pyrrole (0.024 ml, 0.34 mmol) in 70 ml of methylene chloride is transferred to a flask containing anhydrous p-toluenesulfonic acid (50 mg). Aliquots are withdrawn periodically and oxidized with DDQ. TLC on the oxidized aliquots are developed using hexane as the eluant. The reaction is stirred for 12 hours. The solution is oxidized with DDQ, neutralized with pyridine, and the solvents are evaporated. The remaining residue is dissolved in hexane (to the extent possible) and chromatographed on silica using hexane as eluant. The first band is collected and evaporated to dryness leaving 2,3,12,13-tetrabromo-5,10,15,20-tetrakis(perfluoropropyl)porphyrin.

B. Preparation of 2,3,12,13-tetrachloro-5,10,15,20-tetrakis(perfluoropropyl)porphyrin The procedure of Example 19A is repeated except that 3,4-dichloro-2,5-bis(2',2',3',3',4',4',4'-heptafluoro-1'-trimethylsilyloxybutyl)pyrrole is used in place of 3,4-dibromo-2,5-bis(2',2',3',3',4',4',4'-heptafluoro-1'-trimethylsilyloxybutyl)pyrrole.

C. Preparation of 2,3,12,13-tetraiodo-5,10,15,20-tetrakis(perfluoropropyl)porphyrin The procedure of Example 19A is repeated except that 3,4-diiodo-2,5-bis(2',2',3',3',4',4',4'-heptafluoro-1'-trimethylsilyloxybutyl)pyrrole is used in place of 3,4-dibromo-2,5-bis(2',2',3',3',4',4',4'-heptafluoro-1'-trimethylsilyloxybutyl)pyrrole.

Example 20

A. Preparation of 2,12-dibromo-5,10,15,20-tetrakis(perfluoropropyl)porphyrin and 2,13-dibromo-5,10,15,20-tetrakis(perfluoropropyl)porphyrin The procedure of Example 19A is repeated except that 3-bromo-2,5-bis(2',2',3',3',4',4',4'-heptafluoro-1'-trimethylsilyloxybutyl)pyrrole is used in place of 3,4-dibromo-2,5-bis(2'2',3',3',4',4',4'-heptafluoro-1'-trimethylsilyloxybutyl)pyrrole. The two isomers are separated by chromatography on silica gel using pentane as eluant.

B. Preparation of 2,12-dichloro-5,10,15,20-tetrakis(perfluoropropyl)porphyrin and 2,13-dichloro-5,10,15,20-tetrakis(perfluoropropyl)porphyrin The procedure of Example 19B is repeated except that 3-chloro-2,5-bis(2',2',3',3',4',4',4'-heptafluoro-1'-trimethylsilyloxybutyl)pyrrole is used in place of 3,4-dichloro-2,5-bis(2'2',3',3',4',4',4'-heptafluoro-1'-trimethylsilyloxybutyl)pyrrole. The two isomers are separated by chromatography on silica gel using pentane as eluant.

C. Preparation of 2,12-diiodo-5,10,15,20-tetrakis(perfluoropropyl)porphyrin and 2,13-diiodo-5,10,15,20-tetrakis(perfluoropropyl)porphyrin The procedure of Example 19C is repeated except that 3-iodo-2,5-bis(2',2',3',3',4',4',4'-heptafluoro-1'-trimethylsilyloxybutyl)pyrrole is used in place of 3,4-diiodo-2,5-bis(2'2'3',3',4',4',4'-heptafluoro-1'-trimethylsilyloxybutyl)pyrrole. The two isomers are separated by chromatography on silica gel using pentane as eluant.

Example 21

A. Preparation of 2-bromo-5,10,15,20-tetrakis(perfluoropropyl)porphyrin

A solution containing 3-bromo-2,5-bis(2',2',3',3',4',4',4'-heptafluoro-1'-trimethylsilyloxybutyl)pyrrole (0.34 mmol), pyrrole (0.048 ml, 0.68 mmol) and 2,5-bis(2',2',3',3',4',4',4'-heptafluoro-1'-trimethylsilyloxybutyl)pyrrole (0.34 mmol) in 150 ml of methylene chloride is transferred to a flask containing anhydrous p-toluenesulfonic acid (50 mg). Aliquots are withdrawn periodically and oxidized with DDQ. TLC on the oxidized aliquots are developed using hexane as the eluant. The reaction is stirred for 12 hours. The solution is oxidized with DDQ, neutralized with pyridine, and the solvents are evaporated. The remaining residue is dissolved in hexane (to the extent possible) and the product is separated from the unbrominated and dibrominated porphyrin products by chromatography on silica using hexane as eluant.

B. Preparation of 2-chloro-5,10,15,20-tetrakis(perfluoropropyl)porphyrin

The procedure of Example 21A is repeated except that 3-chloro-2,5-bis(2',2',3',3',4',4',4'-heptafluoro-1'-trimethylsilyloxybutyl)pyrrole is used in place of 3-bromo-2,5-bis(2',2',3',3',4',4',4'-heptafluoro-1'-trimethylsilyloxybutyl)pyrrole.

C. Preparation of 2-iodo-5,10,15,20-tetrakis(perfluoropropyl)porphyrin

The procedure of Example 21A is repeated except that 3-iodo-2,5-bis(2',2',3',3',4',4',4'-heptafluoro-1'-trimethylsilyloxybutyl)pyrrole is used in place of 3-bromo-2,5-bis(2',2',3',3',4',4',4'-heptafluoro-1'-trimethylsilyloxybutyl)pyrrole.

Example 22

Preparation of 3,4-disubstituted-2,5-bis(2',2',3',3',4',4',4'-heptafluoro-1'-trimethylsilyloxybutyl)pyrrole)

Palladium catalyzed cross-coupling is performed between 3,4-dibromo-2,5-bis(2',2',3',3',4',4',4'-heptafluoro-1'-hydroxybutyl)pyrrole and a suitably-substituted metal reagent (e.g., R-MgX, R-ZnX, R-borate, R-SnR$_3$) according to the procedure described by Bray, et al., *J. Org. Chem.* 1990, 55, 6317–6328.

Example 23

Preparation of 3-substituted-2,5-bis(2',2',3',3',4',4',4'-heptafluoro-1'-trimethylsilyloxybutyl)pyrrole)

Palladium catalyzed cross-coupling is performed between 3-bromo-2,5-bis(2',2',3',3',4',4',4'-heptafluoro-1'-hydroxybutyl)pyrrole and a suitably-substituted metal reagent (e.g., R-MgX, R-ZnX, R-borate, R-SnR$_3$) according to the procedure described by Bray, et al., *J. Org. Chem.* 1990, 55, 6317–6328.

Example 24

Preparation of [2,3,12,13-tetrakis(perfluorophenyl)-5,10,15,20-tetrakis(perfluoropropyl)porphyrinato]zinc(II)

[2,3,12,13-Tetrabromo-5,10,15,20-tetrakis(perfluoropropyl)porphyrinato]zinc(II) (0.2 mmol), pentafluorophenylzinc bromide (10 mmol), and bis(diphenylphosphino)ferrocene palladium (0.02 mmol) are dissolved in 10 ml of dry THF and the solution is stirred at room temperature under nitrogen. Aliquots are withdrawn periodically and analyzed by TLC on silica gel. Upon completion of the reaction (as indicated by the appearance of a spot on the TLC plate that fluoresces under long-wavelength UV light) the solvent is removed and the mixture is chromatographed on silica gel using hexane as eluant. The fluorescent band is isolated and the solvent is evaporated to leave [2,3,12,13-tetrakis(perfluorophenyl)-5,10,15,20-tetrakis(perfluoropropyl)porphyrinato]zinc(II).

Example 25

Preparation of a chiral, nonstrapped porphyrin oxidation catalyst

[2,3,12,13-Tetrabromo-5,10,15,20-tetrakis(perfluoropropyl)porphyrinato]zinc(II) (0.2 mmol), 2,6-dimethoxyphenylzinc chloride (10 mmol), and bis(diphenylphosphino)ferrocene palladium (0.02 mmol) are dissolved in 10 ml of dry THF and the solution is stirred at room temperature under nitrogen. Aliquots are withdrawn periodically and analyzed by TLC on silica gel. Upon completion of the reaction (as indicated by the appearance of a spot on the TLC plate that fluoresces under long-wavelength UV light) the solvent is removed and the mixture is chromatographed on silica gel using hexane as eluant. The fluorescent band is isolated and the solvent is evaporated to leave ([2,3,12,13-tetrakis(2,6-dimethoxyphenyl)-5,10,15,20-tetrakis(perfluoropropyl)porphyrinato]zinc (II). The porphyrin is treated with 0.9 equivalents of boron triiodide in methylene chloride to remove one methyl group (of the eight). The reaction mixture is chromatographed on silica gel using hexane as eluant. The isolated monohydroxy compound (a racemic mixture) is enantiomerically resolved by recrystallization in the presence of a chiral alkaloid (such as quinine) or by chiral stationary phase HPLC.

Example 26

Preparation of an electron deficient face-to-face porphyrin dimer

[2-Bromo-5,10,15,20-tetrakis(perfluoropropyl)porphyrinato]zinc(II) (0.2 mmol), 1,8-anthracenedizinc chloride (0.1 mmol), and bis(diphenylphosphino)ferrocene palladium (0.02 mmol) are dissolved in 5 ml of dry THF and the solution is stirred at room temperature under nitrogen. Aliquots are withdrawn periodically and analyzed by TLC on silica gel. Upon completion of the reaction (as indicated by the disappearance of a spots on the TLC plate that corresponds to the starting materials) the solvent is removed and the mixture is chromatographed on silica gel using hexane as eluant. The product band is isolated and the solvent is evaporated to leave 1,8-bis[2'-(5',10',15',20'-tetrakis(perfluoropropyl)porphyrinato(Zn)]anthracene.

Example 27

A. Preparation of 2,3,7,8,12,13,17,18-octabromo-5,10,15,20-tetrakis(perfluoropropyl)porphyrin 3,4-Dibromopyrrole (1 mmol) and 3,4-dibromo-2,5-bis(2',2',3',3',4',4',4'-heptafluoro-1'-trimethylsilyloxybutyl)pyrrole (1 mmol) are dissolved in 200 ml of $CH_2Cl_2$ and transferred by canula to a flask containing 100 mg of p-toluenesulfonic acid. Aliquots are withdrawn periodically and oxidized with DDQ. TLC on the oxidized aliquots are developed using hexane as the eluant. The reaction is stirred for 12 hours. The solution is oxidized with DDQ, neutralized with pyridine, and the solvents are evaporated. The remaining residue is dissolved in hexane (to the extent possible) and the product is separated from the nonporphyrin products by chromatography on silica using hexane as eluant.

B. Preparation of 2,3,7,8,12,13,17,18-octachloro-5,10,15,20-tetrakis(perfluoropropyl)porphyrin The procedure of Example 27A is repeated except that 3,4-dichloro-2,5-bis(2',2',3',3',4',4',4'-heptafluoro-1'-trimethylsilyloxybutyl)pyrrole and 3,4-dichloropyrrole are used in place of 3,4-dibromo-2,5-bis(2',2',3',3',4',4',4'-heptafluoro-1'-trimethylsilyloxybutyl)pyrrole and 3,4-dibromopyrrole.

C. Preparation of 2,3,12,13-Tetrabromo-7,8,17,18-tetrachloro-5,10,15,20-tetrakis(perfluoropropyl)porphyrin The procedure of Example 27A is repeated except that 3,4-dichloropyrrole is used in place of 3,4-dibromopyrrole.

D. Preparation of 2,3,12,13-Tetraiodo-7,8,17,18-tetrabromo-5,10,15,20-tetrakis(perfluoropropyl)porphyrin The procedure of Example 27A is repeated except that 3,4-diiodopyrrole is used in place of 3,4-dibromopyrrole.

E. Preparation of 2,3,12,13-Tetraiodo-7,8,17,18-tetrachloro-5,10,15,20-tetrakis(perfluoropropyl)porphyrin The procedure of Example 27D is repeated except that 3,4-dichloro-2,5-bis(2',2',3',3',4',4',4'-heptafluoro-1'-trimethylsilyloxybutyl)pyrrole is used in place of 3,4-dibromo- 2,5-bis(2',2',3',3',4',4',4'-heptafluoro-1'-trimethylsilyloxybutyl)pyrrole.

Example 28

Preparation of 2-(2',2',3',3',4',4',4'-heptafluoro-1'-tosylbutyl)pyrrole

A solution of 2-(2',2',3',3',4',4',4'-heptafluoro-1'-hydroxybutyl)pyrrole (2.6514 g, 10 mmol) dissolved in 25 ml of dry THF is transferred by canula to a suspension of sodium hydride (0.2640 g, 11 mmol) in 50 ml of THF. The mixture is stirred for 2 hours at room temperature. A solution of tosylchloride (11 mmol) in 10 ml of THF is added dropwise and the solution stirred overnight. The resulting suspension is evaporated almost to dryness and 50 ml of water is added. The mixture was extracted 3×50 mL with pentane and the organic layers were combined and dried over magnesium sulfate. The mixture is filtered and the solvent evaporated to yield the product 2-(2',2',3',3',4',4',4'-heptafluoro-1'-tosylbutyl)pyrrole.

Example 29

Preparation of bis-1-(2'-pyrrolyl)-1-perfluoropropylmethane

A solution of 2-(2',2',3',3',4',4',4'-heptafluoro-1'-tosylbutyl)pyrrole (10 mmol) dissolved in 25 ml of dry THF. Dry pyrrole (40 mmol) is added and the solution is brought to reflux under $N_2$ for a period of 6 hours. The solution is brought to room temperature with continued stirring and the volatiles removed under vacuum. The solid is extracted with $CH_2Cl_2$, pumped dry, and chromatographed on silica to give bis-1-(2'-pyrrolyl)-1-perfluoropropylmethane.

Example 30

Preparation of 1,12-perfluoropropyl-1,12-(2'-pyrrolyl)-1,12-tosyl-2,2,3,3,4,4,5, 5,6,6,7,7,8,8,9,9, 10,10,11,11-eicosfluorododecane The reaction is carried out as in Example 1, except that the starting aldehyde is eicosfluorododecyl-1,12-dial dihydrate. 1,12-Perfluoropropyl-1,12-(2'-pyrrolyl)-1,12-hydroxy-2,2, 3,3,4,4, 5,5,6,6,7,7,8,8,9,9,10,10,11,11-eicosfluorododecane is isolated as an oil, dissolved in THF and reacted with tosylchloride as in Example 28 to give desired product.

Example 31

Preparation of 1,12-bis(2'-pyrrolyl)-2,2,3,3,4,4,5,5, 6,6,7,7,8,8,9,9,10,10,11,11-eicosfluorododecane 1,12-Perfluoropropyl-1,12-(2'-pyrrolyl)-1,12-tosyl-2,2,3, 3,4,4,5,5,6,6,7,7,8,8,9,9,10,10,11,11-eicosfluorododecane is reacted with pyrrole as in Example 29. Removal of solvent followed by chromatography on silica gel yields the desired product.

Example 32

Preparation of 1,12-bis[5'-10,15,20-tri (perfluoropropyl)porphyrin]-2,2,3,3,4,4,5,5,6,6,7,7, 8,8,9,9,10,10,11,11-eicosfluorododecane 1,12-Perfluoropropyl-1,12-(2'-pyrrolyl)-1,12-tosyl-2,2,3, 3,4,4,5,5,6,6,7,7,8,8,9,9,10,10,11,11-eicosfluorododecane is reacted with 2-(2',2',3',3',4',4',4'-heptafluoro-1-hydroxybutyl)pyrrole under conditions similar to that described in Example 7. The product, 1,12-bis(5'-10,15,20-perfluoropropylporphyrin)-2,2,3,3,4,4,5,5,6,6,7,7,8,8,9,9, 10,10,11,11-eicosfluorododecane is isolated following chromatography on silica gel.

Example 33

Preparation of 1,12-[5',15'-10',20'-di (perfluoropropyl)porphyryl]-2,2,3,3,4,4,5,5,6,6,7,7, 8,8,9,9,10,10,11,11-eicosfluorododecane 1,12-Bis(2'-pyrrolyl)-2,2,3,3,4,4,5,5,6,6,7,7,8,8,9,9,10, 10-11,11-eicosfluorododecane is reacted with 2 equivalents of heptalfluorobutyraldehyde hydrate and excess sodium hydroxide under conditions similar to Example 3. After a similar work up, the isomeric products are dissolved dry benzene and undergo a p-toluenesulfonic acid-catalyzed reaction under conditions similar to that described in Example 7. After a work up again similar to that described in Example 7, the product strapped porphyrin obtained from an intramolecular condensation is separated from those products derived from intermolecular reactions by silica gel chromatography.

Example 34

Preparation of 1,12-[5',15'-10',20'-porphyryl]-bis(2, 2,3,3,4,4,5,5,6,6,7,7,8,8,9,9,10,10,11,11-eicosfluorododecane 1,12-Bis(2'-pyrrolyl)-2,2,3,3,4,4,5,5,6,6,7,7,8,8,9,9,10, 10,-11,11-eicosfluorododecane is reacted with eicosfluorododecyl-1,12-dial dihydrate under conditions similar to Example 30. As in Example 30, the tetrapyrrolic compound is isolated as the ditosyl derivative and is purified by silica gel chromatography. The material is converted to the product bis-strapped porphyrin and purified utilizing a procedure similar to that described in Example 33.

Example 35

Preparation of a perfluorocarbon-strapped porphyrin with a potential axial ligand for (porphyrinato) metal complexes. (An example of an electron-deficient porphyrin featuring a perfluorcarbon strap linking the porphyrin 5- and 15-(meso) positions and a perfluorocarbon strap incorporating an axial ligand linking the porphyrin 10- and 20-positions.)

1,12-Bis(2'-pyrrolyl)-2,2,3,3,4,4,5,5,6,6,7,7,8,8,9,9,10, 10,11,11 eicosfluorododecane is reacted with 2,5-bis(1',1', 2',2',3',-3',4',4'-octafluorpentyl-5'-al)pyridine dihydrate under conditions similar to Example 30. As in Example 30, the tetrapyrrolic compound is isolated as the ditosyl derivative and is purified by silica gel chromatography. The material is converted to the product bis-strapped porphyrin and purified utilizing a procedure similar to that described in Examples 33 and 34.

Example 36

Preparation of 2-(2",2",3",3",4",4",4"-heptafluoro-1"-hydroxybutyl)dipyrrylmethane Dipyrrylmethane is reacted with heptafluorobutyraldehyde hydrate in a concentrated benzene solution under conditions similar to that described in Example 1. A similar work up followed by silica gel chromatography yields the product 2-(2',2',3',3',4',4',4'-heptafluoro-1'-hydroxybutyl) dipyrrylmethane.

Example 37

Preparation of 2,2'-bis(2",2",3",3",4",4",4"-heptafluoro-1"-hydroxybutyl)dipyrrylmethane Dipyrrylmethane is reacted with heptafluorobutyraldehyde hydrate in a concentrated benzene solution under conditions similar to that described in Example 3. A similar work up followed by silica gel chromatography yields the product 2,2'-bis(2",2",3",3",4",4",4"-heptafluoro-1"-hydroxybutyl)dipyrrylmethane.

Example 38

Preparation of 5,15-diperfluoropropylporphyrin from 2-(2",2",3",3",4",4",4"-heptafluoro-1"-hydroxybutyl)dipyrrylmethane 2-(2",2",3",3",4",4",4"-Heptafluoro-1"-hydroxybutyl) dipyrrylmethane is reacted with itself under conditions similar to that described in Example 7. Purification of the product porphyrin is also accomplished in a similar manner as well to give 5,15-diperfluoropropylporphyrin.

Example 39

Preparation of 5,15-diperfluoropropylporphyrin from 2,2'-bis(2",2",3",3",4",4",4"-heptafluoro-1"-hydroxybutyl)dipyrrylmethane 2,2'-Bis(2",2",3",3",4",4",4"-heptafluoro-1"-hydroxybutyl)dipyrrylmethane is reacted with dipyrrylmethane under conditions similar to that described in Example 14. A similar work up and purification gives 5,15-diperfluoropropylporphyrin.

Example 40

Preparation of 1,12-(2',2"-dipyrrylmethyl)-2,2,3,3,4, 4,5,5,6,6,7,7,8,8,9,9,10,10,11,11-eicosfluorododecane Dipyrrylmethane is reacted with eicosfluorododecyl-1, 12-dial dihydrate under conditions similar to Example 1, except that the reaction is run in benzene to minimize the oligomeric side products. The product dipyrryl species, 1,12-(2',2"-dipyrrylmethyl)-2,2,3,3,4,4,5,5,6,6,7,7,8,8,9,9, 10,10,11,11-eicosfluorododecane is isolated utilizing silica gel chromatography.

Example 41

Preparation of 1,12-(5',15'-porphyryl)-2,2,3,3,4,4,5, 5,6,6,7,7,8,8,9,9,10,10,11,11-eicosfluorododecane 1,12-(2',2"-Dipyrrylmethyl)-2,2,3,3,4,4,5,5,6,6,7,7,8,8,9, 9,10,10,11,11-eicosfluorododecane is reacted with dipyrryl methane and subsequently purified as described in Example 39 to give the product 1,12-(5',15'-prophyryl)-2,2,3,3,4,4,5, 5,6,6,7,7,8,8,9,9,10,10,11,11-eicosfluorododecane.

Example 42

A. Preparation of 1,12-(5',15'-10,20-dibromoporphyryl)-2,2,3,3,4,4,5,5,6,6,7,7,8,8,9,9,10, 10,11,11-eicosfluorododecane 1,12-(5',15'-Porphyryl)-2,2,3,3,4,4,5,5,6,6,7,7,8,8,9,9,10, 10,11,11-eicosfluorododecane is reacted with N-bromosuccinimide (NBS) in dry $CH_2Cl_2$ containing excess pyridine. The mixture is stirred at room temperature for two hours and the solvents evaporated. The remaining solid is treated with aqueous sodium bicarbonate solution and $CHCl_3$ and separated. An additional extraction is carried out with $CHCl_3$. The organic layers are dried over sodium sulfate, the solvent evaporated and the material is chromatographed on silica to enable the separation of the mono- and bis-halogenated porphyrins.

B. Preparation of 1,12-(5',15'-10,20-dichloroporphyryl)-2,2,3,3,4,4,5,5,6,6,7,7,8,8,9,9,10, 10,11,11-eicosfluorododecane The procedure of Example 42A is repeated except that NCS is used in place of NBS.

C. Preparation of 1,12-(5',15'-10,20-diiodoporphyryl)-2,2,3,3,4,4,5,5,6,6,7,7,8,8,9,9,10, 10,11,11-eicosfluorododecane The procedure of Example 42A is repeated except that NIS is used in place of NBS.

Example 43

A. Preparation of 5,15-bisperfluoropropyl-10,20-dibromoporphyrin 5,15-diperfluoropropylporphyrin is reacted with N-bromosuccinimide (NBS) in dry $CH_2Cl_2$ containing excess pyridine. The mixture is stirred at room temperature for two hours and the solvents evaporated. The remaining solid is treated with aqueous sodium bicarbonate solution and $CHCl_3$ and separated. An additional extraction is carried out with $CHCl_3$. The organic layers are dried over sodium sulfate, the solvent evaporated and the material is chromatographed on silica to enable the separation of the mono- and bis-halogenated porphyrins.

B. Preparation of 5,15-bisperfluoropropyl-10,20-dichloroporphyrin

The procedure of Example 43A is repeated except that NCS is used in place of NBS.

C. Preparation of 5,15-bisperfluoropropyl-10,20-diiodoporphyrin

The procedure of Example 43A is repeated except that NIS is used in place of NBS.

Example 44

Preparation of 2,3-bisperfluoromethylpyrrole from 1-triisopropylsilyl-2,3-dibromopyrrole 1-Triisopropylsilyl-2,3-dibromopyrrole is reacted with a twenty-fold molar excess of trifluoromethylzinc chloride in the presence of 5 mole percent $Pd(PPh_3)_4$ in tetraglyme at 100° C. The reaction is monitored by TLC. After 48 hours, the reaction is quenched with water, the solvents removed, and the material is chromatographed on silica to yield 1-triisopropylsilyl-2,3-diperfluoromethylpyrrole. This material is desilylated with tetrabutylammonium fluoride and then used immediately in a porphyrin condensation reaction.

Example 45

Preparation of 1,6-(3',4'-pyrrolyl)-1,1,2,2,3,3,4,4,5, 5,6,6-dodecafluorohexane

Similar to that described in Example 44, a dilute solution of 1-triisopropylsilyl-2,3-dibromopyrrole is reacted with one equivalent of 1,6-bis(chlorozincyl)-1,1,2,2,3,3,4,4,5,5, 6,6-dodecafluorohexane in tetraglyme in the presence of Pd catalyst for one week at 100° C. Work up is as described in Example 44 above.

Example 46

Preparation of 1,6-(3',4'-pyrrolyl)-1,1,2,2,3,3,4,4,5, 5,6,6-dodecafluorohexane from pyrrole and perfluorocyclooctyl-4-yne Pyrrole and perfluorocyclooctyl-4-yne are reacted in $CHCl_3$ under conditions appropriate to induce a Diels-Alder reaction between the two reactants that is followed by a reverse Diels-Alder reaction that extrudes acetylene.

Example 47

Preparation of 1,6-[2'-(2",2",3",3",4",4",4"-heptafluoro-1"-hydroxybutyl)-3',4'-pyrrolyl]-1,1,2,2, 3,3,4,4,5,5,6,6-dodecafluorohexane 1,6-(3',4'-Pyrrolyl)-1,1,2,2,3,3,4,4,5,5,6,6-octafluorohexane is reacted with heptafluorobutyraldehyde hydrate according to the procedure outlined in Example 1; purification and isolation are accomplished according to the general scheme outlined in Example 1 as well.

Example 48

Preparation of 2,5-bis(2',2',3',3',4',4',4'-heptafluoro-1'-trimethylsiloxybutyl)-3-trifluoromethylpyrrole Trifluoromethylzinc chloride is reacted with 3-bromo-2, 5-bis(2,2,3,3,4,4-heptafluoro-1-trimethylsilyloxybutyl)

Example 49

Preparation of 2-(2',2',3',3',4',4',4'-heptafluoro-1'-trimethylsiloxybutyl)-3-trifluoromethylpyrrole 2-(2',2',3',3',4',4',4'-Heptafluoro-1'-trimethylsiloxybutyl) pyrrole is reacted with N-trifluoromethyl-N-nitrosotrifluoromethanesulfonamide under conditions similar to those described by Umemoto, et al., *Bull. Chem. Soc. Jpn.* 1986, 59, 447. Following the recommended work up procedure, the solvent is removed and the organic residue chromatographed on silica to yield 2-(2',2',3',3',4',4',4'-heptafluoro-1'-trimethylsiloxybutyl)-3-trifluoromethylpyrrole.

Example 50

Preparation of 1,12-(2',5'-Pyrrolyl)-1,12-trimethylsiloxy-2,2,3,3,4,4,5,5,6,6,7,7,8,8,9,9,10,10-eicosofluorodecane from eicosfluorododecyl-1,12-dial dihydrate Pyrrole is reacted with one equivalent of eicosfluorododecyl-1,12-dial dihydrate under conditions similar to that described in Example 40. Following a similar work up procedure, silica gel chromatography enables the separation of the product 1",1"-[2',5'-bis(2",2",3",3",4",4",4"-heptafluoro-1"-trimethylsiloxybutyl)pyrrolyl]-2,2,3,3,4,4,5,5,6,6,7,7,8,8,9,9,10,10,11,11-eicosfluorododecane from 1,12-perfluoropropyl-1,12-(2'-pyrrolyl)-1,12-hydroxy- 2,2,3,3,4,4,5,5,6,6,7,7,8,8,9,9,10,10,11,11-eicosfluorododecane and other oligomeric by products. The product is converted to its trimethylsiloxy derivative utilizing an experimental procedure similar to that described in Example 12.

Example 51

Preparation of 1,12-(2',5'-pyrrolyl)-1,12-trimethylsiloxy-2,2,3,3,4,4,5,5,6,6,7,7,8,8,9,9,10,10-eicosofluorodecane from eicosfluorododecyl-1,12-diacid chloride Pyrrole is reacted with one equivalent of eicosfluorododecyl-1,12-diacid chloride in dry THF under nitrogen. The reaction is monitored by TLC. At the reaction endpoint, the solvents are removed and the material chromatographed on silica to give the fluorocarbon-strapped 2,5-dialdehydyl pyrrole. The product is reacted with sodium borohydride in THF, quenched with water and re-chromatographed on silica, isolated, and converted to its trimethylsiloxy derivative utilizing an experimental procedure similar to that described in Example 12 to give the desired product, 1,12-[2',5'-bis(1"-2",2",3",3",4",4",4"-heptafluoro-1"-trimethylsiloxybutyl)pyrrolyl]-2,2,3,3,4,4,5,5,6,6,7,7,8,8,9,9,10,10,11,11-eicosfluorododecane. A large number of pyrrolic precursors suitable for the preparation of perfluorocarbon-strapped porphyrins exist using the condensation methodologies described herein. A number of representative pyrryl and dipyrryl species are described in Examples 53–55.

Example 52

Preparation of cis- and trans-1,12-[5',10'-15',20'-porphyryl]bis(2,2,3,3,4,4,5,5,6,6,7,7,8,8,9,9,10,10,11,11-eicosfluorododecane 1,12-[2',5'-Bis(1"-2",2",3",3",4",4",4"-heptafluoro-1"-trimethylsiloxybutyl)pyrrolyl]-2,2,3,3,4,4,5,5,6,6,7,7,8,8,9,9,10,10,11,11-eicosfluorododecane is reacted with pyrrole under conditions similar to that described in Example 14. At the reaction endpoint, work up follows the procedure outlined in Example 14; the two product porphyrins, cis- and trans-1,12-[5',10'-15',20'-porphyryl]-bis(2,2,3,3,4,4,5,5,6,6,7,7,8,8,9,9,10,10,11,11-eicosfluorododecane) are separated and isolated by chromatography on silica.

Example 53

Preparation of 1,12-bis(3'-pyrrolyl)-2,2,3,3,4,4,5,5,6,6,7,7,8,8,9,9,10,10,11,11-eicosfluorododecane from perfluorocarbonbis(chlorozinc) reagents Excess 3-bromopyrrole is reacted with 1,12-bis(chlorozincyl)-2,2,3,3,4,4,5,5,6,6,7,7,8,8,9,9,10,10,11,11-eicosfluorododecane under conditions similar to that described in Example 45. Work up and chromatographic isolation affords 1,12-bis(3'-pyrrolyl)-2,2,3,3,4,4,5,5,6,6,7,7,8,8,9,9,10,10,11,11-eicosfluorododecane.

Example 54

Preparation of 1,12-bis[3'-2'-(2",2",3",3",4",4",4"-heptafluoro-1"-trimethylsiloxybutyl)pyrrolyl]-2,2,3,3,4,4,5,5,6,6,7,7,8,8,9,9,10,10,11,11-eicosfluorododecane from perfluorocarbonbis(chlorozinc) reagents 4-Bromo-2-(2',2',3',3',4',4',4'-heptafluoro-1'-trimethylsiloxybutyl)pyrrole is reacted with 1,12-bis(chlorozincyl)-2,2,3,3,4,4,5,5,6,6,7,7,8,8,9,9,10,10,11,11-eicosfluorododecane under conditions similar to that described in Example 45. Work up and chromatographic isolation affords 1,12-bis[3'-2'-(2",2",3",3",4",4",4"-heptafluoro-1"-trimethylsiloxybutyl)pyrrolyl]-2,2,3,3,4,4,5,5,6,6,7,7,8,8,9,9,10,10,11,11-eicosfluorododecane

Example 55

Preparation of 1,12-bis[3'-2'-(2",2",3",3",4",4",4"-heptafluoro-1"-trimethylsiloxybutyl)pyrrolyl]-2,2,3,3,4,4,5,5,6,6,7,7,8,8,9,9,10,10,11,11-eicosfluorododecane from 1,12-bis(N'-N-nitrosotrifluoromethanesulfonamide)-2,2,3,3,4,4,5,5,6,6,7,7,8,8,9,9,10,10,11,11-eicosfluorododecane Excess 2-(2',2',3',3',4',4',4'-heptafluoro-1'-trimethylsiloxybutyl)pyrrole is reacted with 1,12-bis(N'-N-nitrosotrifluoromethanesulfonamide)-2,2,3,3,4,4,5,5,6,6,7,7,8,8,9,9,10,10,11,11-eicosfluorododecane under conditions similar to that described for Example 49. Work up and chromatographic separation yields 1,12-bis[3'-2'-(2",2",3",3",4",4",4"-heptafluoro-1"-trimethylsiloxybutyl)pyrrolyl]-2,2,3,3,4,4,5,5,6,6,7,7,8,8,9,9,10,10,11,11-eicosfluorododecane. Straps originating and/or terminating at a pyrrole 3- or 4-position will undoubtedly give rise to a large number of isomers when converted to their 2-(2',2',3',3',4',4',4'-heptafluoro-1'-trimethylsiloxybutyl) derivatives. Cyclization of these materials, the 2,5-bis(2',2',3',3',4',4',4'-heptafluoro-1'-trimethylsiloxybutyl) derivatives or simple perfluorocarbon-linked pyrroles (Example 53) will allow for the formation of mono-strapped porphyrins along with cis and trans-strapped species. A variety of isomeric derivatives of these materials will be present prior to chromatographic separation. One particular advantage of strapping porphyrins at their β-positions is that is leaves the meso positions free for further derivatization.

Example 56

Preparation of Chiral, Nonstrapped Porphyrin Oxidation Catalyst 2,3,12,13-Tetrabromo-5,10,15,20-tetrakis(perfluoropropyl)porphyrinato(zinc) (0.2 mmol), 2,6- dimethoxyphenylzinc chloride (10 mmol), and bis(diphenylphosphino)ferrocene palladium (0.02 mmol) are dissolved in 10 ml of dry THF and the solution is stirred at room temperature under nitrogen. Aliquots are withdrawn periodically and analyzed by TLC on silica gel. When a substantial portion of the material has three bromine atoms exchanged for three aryl moieties, the reaction is quenched by the introduction of air. The solvent is removed and the mixture is chromatographed on silica gel using hexane THF as eluant. The appropriate band is isolated and the solvent is evaporated to leave 2,3,12,-tris(2,6 dimethoxyphenyl)-13-bromo-5,10,15,20-tetrakis(perfluoropropyl)porphyrinato (zinc). The porphyrin is treated with 2-t-butylphenylzinc chloride (10 mmol), and bis(diphenylphosphino)ferrocene palladium (0.02 mmol) dissolved in 10 ml of dry THF and the solution is stirred at room temperature under nitrogen. The reaction mixture is chromatographed on silica gel using hexane as eluant. The isolated a racemic mixture is enantiomerically resolved by recrystallization in the presence of a chiral alkaloid (such as quinine) or by chiral stationary phase HPLC.

Example 57

Preparation of Nonstrapped- and Strapped-porphyrin Oxidation Catalysts

Figure 2:
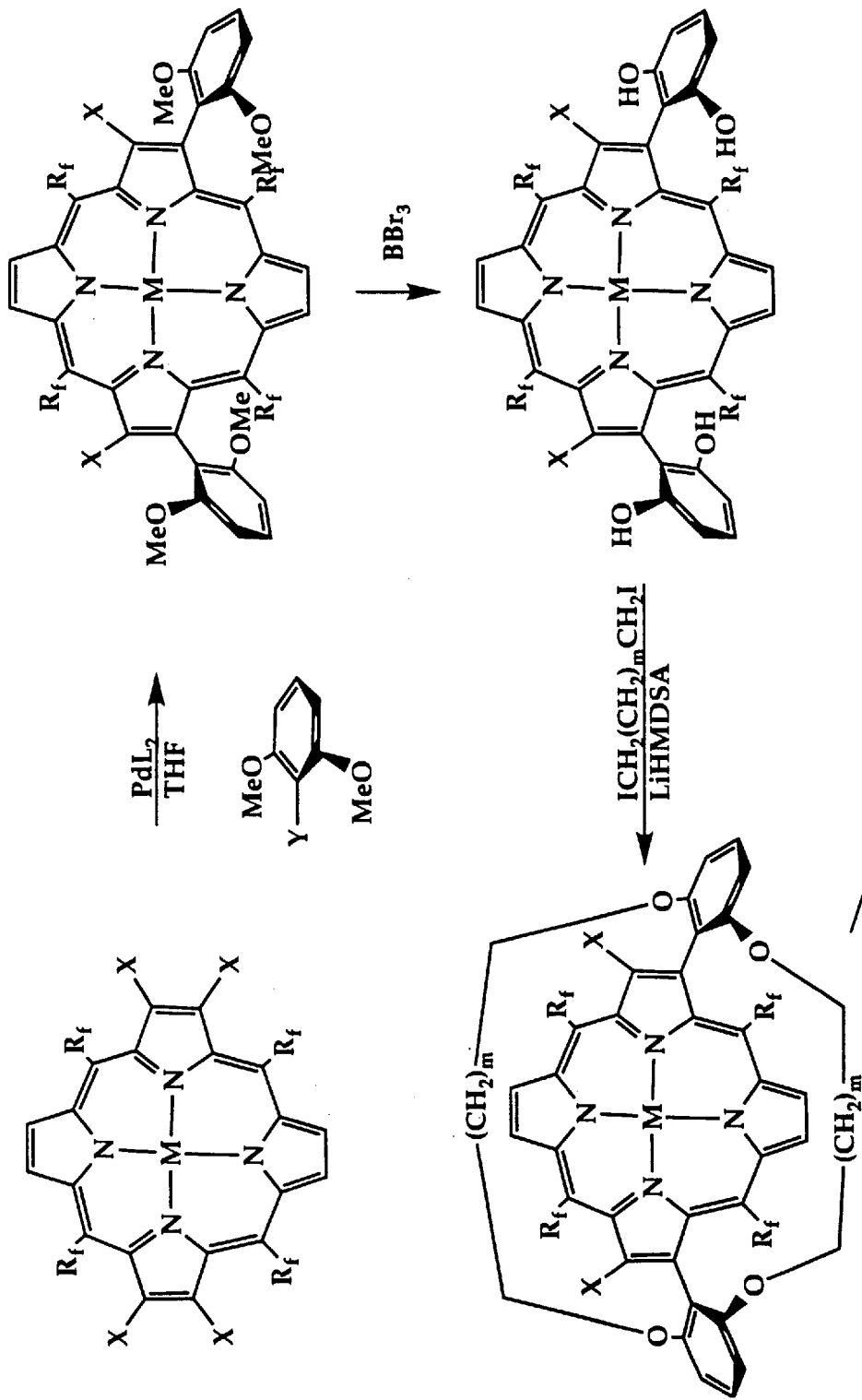
FIG. 2 shows a synthetic scheme for the preparation of doubly-strapped porphyrins.

The isolation of chiral catalysts relies on the demonstrated enhanced solubility imparted by the perfluoroalkyl groups. Porphyrins (such as tetraphenylporphyrin (TPP)) are notoriously difficult to chromatograph. Perfluoroalkyl-substituted porphyrins, on the other hand, are easily purified by normal phase or reverse phase HPLC. Therefore, a wide variety of commercially available chiral chromatography columns are potentially applicable to these compounds, along with their more highly-elaborated derivatives. This capability simplifies the general preparative scheme since racemic mixtures of the catalysts may be prepared and resolved yielding catalysts with opposite stereoselectivity. Two general approaches to asymmetric catalyst synthesis are outlined in FIGS. 1 and 2, wherein: M=Zn or $H_2$; X=Br or I; R=H, O-methyl, O-ethyl, O-isopropyl, Cl, methyl, ethyl, isopropyl, or tert-butyl; Y=ZnCl or $B(OH)_2$; $R_F$=perfluoroalkyl; R'=a group different from R; $L_B$=a phosphorous-, nitrogen- or arsenic-containing Lewis base; and m=4–12. In the first method, shown in FIG. 1, three identical bulky groups are appended to the porphyrin, and the resulting singly halogenated species is isolated. Chirality is imparted by the attachment of the last, unsymmetrically substituted aryl group that also contains an axial ligand tethered to the 2-position. The axial ligand will effectively close off one face of the molecule for epoxidation (or hydroxylation) chemistry. The resulting racemic product can be resolved by chiral HPLC. Resolution can be further enhanced by the addition of chiral amine bases that can act as axial ligands to form diastereomeric complexes for achiral reverse phase media. The second general approach to enantioselective epoxidation (or chiral alkane hydroxylation) catalysts involves the preparation of strapped porphyrins, as outlined in FIG. 2. The advantages to this scheme are that entry to the metal center is extremely restricted and that fluorocarbon containing straps may be used. (The incorporation of chemically inert perfluoroalkyl straps is key if intramolecular reactions are implicated in catalyst degradation.) Molecular models indicate that the nine and ten atom bridges can be accommodated without severely distorting the porphyrin core. Coupling of the final two groups and resolution of the enantiomers will be carried out as above. The effectiveness of the catalysts for enantioselective epoxidations (or selective alkane hydroxylations) can be evaluated by chiral HPLC, optical rotation, and shift reagent NMR techniques. Enantioselectivity as well as absolute product chirality can be monitored as a function of the turnover number to determine if partially degraded, catalytically competent species are formed.

Those skilled in the art will appreciate that numerous changes and modifications may be made to the preferred embodiments of the invention and that such changes and modifications may be made without departing from the spirit of the invention. For example, it is believed that the methods of the present invention can be practiced using porphyrin-related compounds such as chlorins, phorbins, bacteriochlorins, porphyrinogens, sapphyrins, texaphrins, and pthalocyanines in place of porphyrins. It is therefore intended that the appended claims cover all such equivalent variations as fall within the true spirit and scope of the invention.

What is claimed is:

1. A compound having formula (7), (8), or (9):

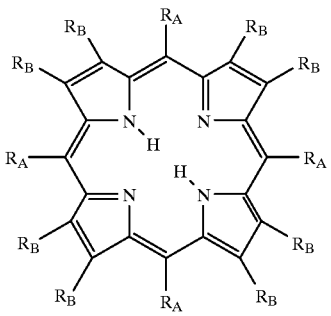

(7)

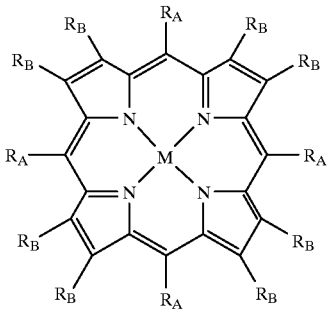

(8)

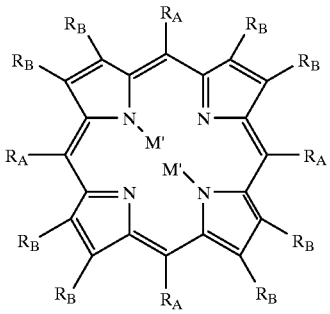

(9)

wherein M and M' are metal atoms and:
at least two $R_A$, together, form a covalently-bound, multi-atom linkage;
at least two $R_B$, together, form a covalently-bound, multi-atom linkage; or at least one $R_A$ and at least one $R_B$, together, form a covalently-bound, multi-atom linkage.

2. A compound having formula (7), (8), or (9):

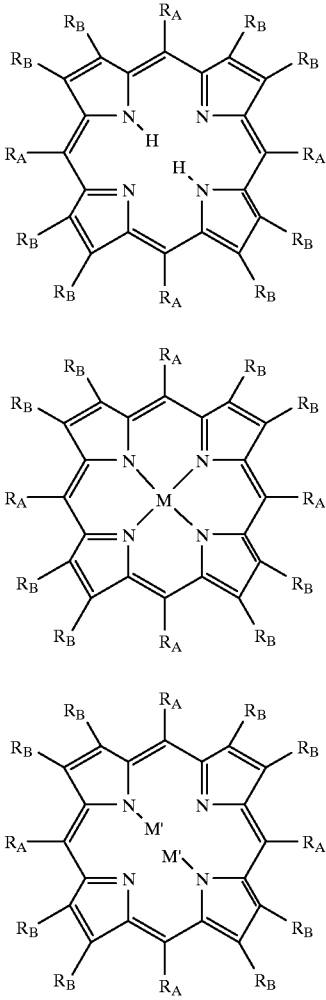

wherein M and M' are metal atoms and:

a single $R_B$ on each pyrryl moiety is a halogen; or both $R_B$ on each of two non-adjacent pyrryl moieties are halogens.

3. In a process in which an alkane is selectively oxidized by contact with air or oxygen in the presence of a catalyst comprising a transition metal coordination complex, the improvement wherein said complex comprises a compound according to claim 1.

4. In a process in which a carbon-carbon double bond is selectively oxidized by contact with air or oxygen in the presence of a catalyst comprising a transition metal coordination complex, the improvement wherein said complex comprises a compound according to claim 1.

5. A supported catalyst comprising a compound according to claim 1 on a solid support material.

6. The compound of claim 1 wherein at least two $R_A$, together, are alkyl having 3 to about 35 carbon atoms, aryl having 6 to about 40 carbon atoms, C(O)O–(alkyl) or C(O)–(alkyl) wherein alkyl groups have from about 1–50 carbon atoms and aryl groups have about 3–75 carbon atoms.

7. The compound of claim 1 wherein at least two $R_A$, together, are haloalkyl having 3 to about 35 carbon atoms or haloaryl having 6 to about 40 carbon atoms.

8. The compound of claim 1 wherein at least two $R_A$, together, are perflluoroalkyl having 3 to about 35 carbon atoms or perfluoroalkyl having 6 to about 50 carbon atoms.

9. The compound of claim 1 wherein at least two $R_B$, together are alkyl having 3 to about 35 carbon atoms, aryl having 6 to about 40 carbon atoms, C(O)O–(alkyl) or C(O)–(alkyl) wherein alkyl groups have from about 1–50 carbon atoms and aryl groups have about 3–75 carbon atoms 10. The compound of claim 1 wherein at least two $R_B$, together, are haloalkyl having 3 to about 35 carbon atoms or haloaryl having 6 to about 40 carbon atoms.

11. The compound of claim 1 wherein at least two $R_B$, together, are perfluoroalkyl having 3 to about 35 carbon atoms or perfluoroaryl having 6 to about 50 carbon atoms.

* * * * *

UNITED STATES PATENT AND TRADEMARK OFFICE
CERTIFICATE OF CORRECTION

| | | |
|---|---|---|
| PATENT NO. | : 5,955,603 | Page 1 of 1 |
| APPLICATION NO. | : 09/167443 | |
| DATED | : September 21, 1999 | |
| INVENTOR(S) | : Therien et al. | |

It is certified that error appears in the above-identified patent and that said Letters Patent is hereby corrected as shown below:

Column 1 at line 15 insert the following phrase, --This invention was made with government support under grant EPS9255225 awarded by United States National Science Foundation. The government has certain rights in the invention.--

Signed and Sealed this

Twenty-sixth Day of February, 2008

JON W. DUDAS
*Director of the United States Patent and Trademark Office*